(12) United States Patent
Zeng et al.

(10) Patent No.: US 11,147,797 B2
(45) Date of Patent: Oct. 19, 2021

(54) PHOTODYNAMIC THERAPEUTIC COMPOUNDS AND PHOTODYNAMIC METHODS OF TREATMENT

(71) Applicant: SALT AND LIGHT PHARMACEUTICALS PTY. LTD., Ferntree Gully (AU)

(72) Inventors: Jun Zeng, Ferntree Gully (AU); Xinyu Tang, Chengdu (CN); James T Palmer, Warrandyte (AU)

(73) Assignee: SALT AND LIGHT PHARMACEUTICALS PTY. LTD., Ferntree Gully (AU)

( * ) Notice: Subject to any disclaimer, the term of this patent is extended or adjusted under 35 U.S.C. 154(b) by 0 days.

(21) Appl. No.: 16/467,024

(22) PCT Filed: Dec. 5, 2017

(86) PCT No.: PCT/AU2017/000257
§ 371 (c)(1),
(2) Date: Jun. 5, 2019

(87) PCT Pub. No.: WO2018/102849
PCT Pub. Date: Jun. 14, 2018

(65) Prior Publication Data
US 2019/0307725 A1 Oct. 10, 2019

(30) Foreign Application Priority Data

Dec. 5, 2016 (AU) ................................ 2016905000
Sep. 27, 2017 (AU) ................................ 2017903924

(51) Int. Cl.
*C07D 487/22* (2006.01)
*A61K 31/409* (2006.01)
*A61P 35/00* (2006.01)
*A61K 41/00* (2020.01)

(52) U.S. Cl.
CPC ........ *A61K 31/409* (2013.01); *A61K 41/0057* (2013.01); *A61P 35/00* (2018.01); *C07D 487/22* (2013.01)

(58) Field of Classification Search
CPC .................................................. C07D 487/22
See application file for complete search history.

(56) References Cited

FOREIGN PATENT DOCUMENTS

WO 1996013504 A1 5/1996
WO 2014025370 A1 2/2014

OTHER PUBLICATIONS

Extended European Search Report for European Application No. 17878695.0 dated Jul. 2, 2020.

International Search Report and Written Opinion of the International Searching Authority for PCT Application No. PCT/AU2017/000257, dated Jan. 19, 2018.
Carrenho, Luise Zozula Blind et al., "Investigation of anti-inflammatory and anti-proliferative activities promoted by photoactivated cationic porphyrin", Photodiagnosis and Photodynamic Therapy, May 22, 2015.
Dogutan, Dilek Kiper et al., "Rational or Statistical Routes from 1-Acyldipyrromethanes to meso-Substituted Porphyrins. Distinct Patterns, Multiple Pyridyl Substituents, and Amphipathic Architectures", The Journal of Organic Chemistry, Aug. 1, 2008.
Meng, Guangzhen G. et al., "Porphyrin chemistry pertaining to the design of anti-cancer drugs; part 2, the synthesis and in vitro tests of water-soluble porphyrins containing, in the meso positions, the functional groups: 4-methylpyridinium, or 4-sulfonatophenyl, in combination with phenyl, 4-pyridyl, 4-nitrophenyl, or 4-amino", Canadian journal of Chemistry, Dec. 1, 1994.
Rapozzi, Valentina et al., "Anticancer activity of cationic porphyrins in melanoma tumor-bearing mice and mechanistic in vitro studies", Molecular Cancer, Apr. 1, 2014.
Rowland, Gerald B et al., "The effect of pyridyl substituents on the thermodynamics of porphyrin binding to G-quadruplex DNA", Bioorganic & Medicinal Chemistry: A Tetrahedron Publication for the Rapid Dissemination of Full Original Research Papers and Critical Reviews on Biomolecular Chemistry, Medicinal Chemistry and Related Disciplines, Sep. 21, 2013.
Achelle, Sylvain et al, "Bisporphyrin connected by pyrimidine: synthesis and photophysical properties," Journal of Porphyrins and Phthalocyanines, 2010, 14, 877-884. Abstract; Compounds 2 and 3, Scheme I.
CAS Registry Number: 777837-42-0, STN Entry Date: Nov. 10, 2004. Whole Document.
Deda, Daiana et al, "Correlation of photodynamic activity and singlet oxygen quantum yields in two series of hydrophobic monocationic porphyrins." Journal of Porphyrins and Phthalocyanines, 2012, 16, 55-63. Abstract; compounds 4Mme and 3Mme; Figures 1-5.
El-Far, Mohamed et al, "A comparative study of 28 porphyrins and their abilities to localize in mammary mouse carcinoma: uroporphyrin I superior to hematoporphyrin derivative." Progress in Clinical and Biological Research, 1984, 170, 661-672. Abstract; p. 663, third paragraph; p. 664, fifth paragraph; p. 665, second paragraph.

(Continued)

*Primary Examiner* — Brian E McDowell
(74) *Attorney, Agent, or Firm* — Budzyn IP Law, LLC

(57) ABSTRACT

The invention provides photodynamic therapeutic compounds and photodynamic methods of treatment. The photodynamic therapeutic compounds may be activated by long wavelength light. The photo-activation by long wavelength light may allow improved tissue penetration. The compounds are selected from the group consisting of compounds of formula (i), or a pharmaceutically acceptable salt thereof: formula (i) wherein PDC is a photodynamic core and wherein R1; R2; R3; and R4 are H, phenyl, pyridine-4-yl, methylpyridinium, N-methylpyridinium-3-yl; 2-phenyl-N-methylpyridinium-4-yl, 3-phenyl-N-methylpyridinium-4-yl, 4-phenyl-N-methylpyridinium-4-yl, 2-phenyl-N-methylpyridinium-3-yl, 3-phenyl-N-methylpyridinium-3-yl or 4-phenyl-N-methylpyridinium-3-yl; and wherein any one or more of R1, R2, R3 and R4 may be optionally substituted.

7 Claims, 20 Drawing Sheets

(56) References Cited

OTHER PUBLICATIONS

Engelmann, Fabio et al, "Interaction of cationic meso-porphyrins with liposomes, mitochondria and erythrocytes." Journal of Bioenergetics and Biomembranes, 2007, 39(2), 175-185. Abstract; Scheme I; p. 179, left-hand column, last paragraph; p. 182.
Gonçalves, Diana et al, "Synthesis and G-quadruplex binding studies of new 4-N-methylpyridinium porphyrins." Organic and Biomolecular Chemistry, 2006, 4(17), 3337-3342. Abstract; Figure I; Table 1.
Jin, Shu Fang et al, "Synthesis, G-quadruplexes DNA binding, and photocytotoxicity of novel cationic expanded porphyrins." Bioorganic Chemistry, 2015, 60, 110-117. Abstract; Compounds 1-3, Figure 2; Table 3.
Photodynamic Therapy—Wikipedia [retrieved from internet Jan. 4, 2018] <URL: https://en.wikipedia.org/wiki/Photodynamic_therapy> published on May 16, 2004 as per Wayback Machine Whole document.
Varamo, Marilyne et al, "Development of Strategies for the Regiocontrolled Synthesis of meso-5, 10, 20-Triaryl-2, 3-chlorins." Organic Letters, 2007, 9(23), 4689-4692. Abstract, Schemes 1-3.
Zakavi, Saeed et al, "Effects of Core and/or Peripheral Protonation of meso-Tetra(2-, 3-, and 4-pyridyl) Porphyrin and meso-Tetra (3-methylpyridyl) Porphyrin on Their UV-vis Spectra." Journal of Spectroscopy, 2013, Article ID 713745. Abstract; Figures 1-3; Tables 1-6.
Zhao, Ping et al, "G-quadruplex DNA interactions, docking and cell photocytotoxicity research of porphyrin dyes." Dyes and Pigments, 2016, 128, 41-48. Abstract; Figures 1, 5, 9, and 10; Table 2.

Representative Compound 10

| Wavelength (nm) | Color Range | Penetration |
|---|---|---|
| 150-380 | UV | <0.1 |
| 390-470 | Violet to Deep Blue | ~0.3 |
| 475-545 | Blue-Green | ~0.3-0.5 |
| 545-600 | Yellow to Orange | ~0.5-1.0 |
| 600-650 | Red | ~1.0-2.0 |
| 650-950 | Deep Red-NIR | 2-3 |
| 950-1200 | NIR | 1 |

PHOTODYNAMIC THERAPEUTIC COMPOUNDS AND PHOTODYNAMIC METHODS OF TREATMENT

FIELD OF THE INVENTION

The present invention relates to therapeutic compounds and methods of treatment. More particularly, the present invention relates to photodynamic therapeutic compounds and photodynamic methods for the treatment of a cancer, disease, disorder or condition.

BACKGROUND TO THE INVENTION

Photodynamic therapy (PDT) involves the administration of a photosensitizer (PS) either systemically or locally, followed by illumination with visible light (Huang Z et al., Technol. Cancer Res. Treatment, 2008, 7:309-320). The PS absorbs light and, in the presence of oxygen, transfers the energy, producing cytotoxic oxygen species which can be used to treat cancer cells and other diseases.

Unlike chemotherapy and radiotherapy, PDT involves the combination of two agents: light and PS. Compared with conventional chemotherapy and radiotherapy, PDT has the advantage of less toxicity. There are two key components involved in the efficacy of a PS: 1) wavelength of light; and 2) specificity to the target. Currently, the photosensitisers on the market have absorption wavelengths of up to 750 nm (Castano A P et al., Photodiagnosis Photodyn. Ther. 2004 1:279-93). Additionally, their application has been limited on the surface of the human body, such as those that can only be used for the treatment of cancers in close proximity to the skin such as, skin cancer and lung cancer etc. Moreover, the issues relating to the specificity of PSs to treat cancer cells have not been well addressed. The result of which is that the patient has to avoid sun light for a significant time after the treatment.

To advance the treatment of common cancer types, a new generation of PS is needed with both a long wavelength activation and selectivity to specific protein targets involved in specific cancers.

Recent development has been made in provisions of PSs with a long-wavelength activation up to 700 to 800 nm, in order to achieve improved tissue penetration, minimal dark toxicity but high photocytotoxicity, water solubility and rapid clearance from the body (Castano A P et al., Photodiagnosis Photodyn. Ther. 2004 1:279-93; Caetano A P et al Photodiagn. Photodyn. Ther. 2005, 2:91).

Until now, the specificity of PSs towards cancer cells remains unaddressed. One of the common targets identified in human cancers is the oncogenic Ras protein (Fernandez-Medarde A. Santos E., Gene and Cancer, 2(3) 344, 2011). Members of the Ras superfamily of small GTPases regulate many cellular functions, including control of protein transport, cytoskeletal regulation, and cell growth (McCormick F. & Wittinghofer A., Curr. Opin. Biotech. 1996, 7:449). Ras protein activates several signalling pathways, and oncogenic mutants of Ras protein are detected in around 30% of many human cancers (Barbacid M, Annu. Rev. Biochem. 1987, 56:779). Raf-1 is one of the immediate downstream targets of Ras, promoting Ras-dependent activation of the MAP kinase (mitogen activated protein kinase) pathway, which triggers cell growth and differentiation. Interactions of Ras with Raf are mediated by two domains of Ras, including Ras binding domain in the N-terminus of Ras, which binds directly to the GTP (guanosine triphosphate)-bound form of Ras (Barbacid M, Annu. Rev. Biochem. 1987, 56:779). Ras in its GDP (guanosine di-phosphate)-bound form, or "off" state does not bind to Ras. Oncogenic Ras exists only in active form, resulting in a constitutive activation of Ras-mediated signalling events and promoting aberrant growth of human tumours. Antagonists of Ras-Raf interactions are likely to inhibit the Ras-stimulated signal transduction pathway.

The development of inhibitors targeting Ras protein in order to block Ras-Raf interactions has presented significant challenges for drug discovery. At least in part because the Ras binding domain (RBD) of Raf binds to a less-defined surface region of Ras protein (Switch I: residues 30-40). Traditionally, drug development targeting Ras protein focuses on the drug to prevent activated Ras from reaching the plasma membrane. An example of such a drug is Salirasib. Salirasib is a farnesyl mimic that competes with active Ras for binding to the oncoprotein's docking protein, galectin, on the plasma membrane, leading to degradation of active cytoplasmic Ras. Salirasib has shown promising results in a clinical trial for pancreatic cancer (Baker N M and Der C J, Nature 2013, 497:577-578). Although significant progress has been made in understanding Ras-Raf binding and in development of inhibitors that disrupt the Ras-Raf binding, the best inhibitors for Ras-Raf interactions currently available have only shown $IC_{50}$ inhibitory activities of around 10-30 µM (Shima F et al., PNAS, 2013, 110:8182).

The reference to any prior art in this specification is not, and should not be taken as, an acknowledgement or any form of suggestion that the prior art forms part of the common general knowledge.

SUMMARY OF THE INVENTION

Generally, embodiments of the present invention relate to photodynamic therapeutic compounds and photodynamic methods of treatment.

In a broad form, the present invention relates to photodynamic therapeutic compounds and photodynamic methods of treatment for cancer, or an associated disease, disorder or condition. The photodynamic therapeutic compounds may be activated by long wavelength light. The photoactivation by long wavelength light may allow improved tissue penetration.

In one aspect, although it need not be the only or indeed the broadest aspect, the invention resides in a compound selected from the group consisting of compounds of formula (i), or a pharmaceutically acceptable salt thereof:

formula (i)

wherein PDC is a photodynamic core and
wherein
R1 is H, phenyl, pyridin-4-yl, methylpyridinium, N-methylpyridinium-3-yl; 2-phenyl-N-methylpyridinium-4-yl, 3-phenyl-N-methylpyridinium-4-yl, 4-phenyl-N-methylpyridinium-4-yl, 2-phenyl-N-methylpyridinium-3-yl, 3-phenyl-N-methylpyridinium-3-yl or 4-phenyl-N-methylpyridinium-4-yl;
R2 is H, phenyl, pyridin-4-yl, methylpyridinium, N-methylpyridinium-3-yl; 2-phenyl-N-methylpyridinium-4-yl, 3-phenyl-N-methylpyridinium-4-yl, 4-phenyl-N-methylpyridinium-4-yl, 2-phenyl-N-methylpyridinium-3-yl, 3-phenyl-N-methylpyridinium-3-yl or 4-phenyl-N-methylpyridinium-4-yl;

R3 is H, phenyl, pyridin-4-yl, methylpyridinium, N-methylpyridinium-3-yl; 2-phenyl-N-methylpyridinium-4-yl, 3-phenyl-N-methylpyridinium-4-yl, 4-phenyl-N-methylpyridinium-4-yl, 2-phenyl-N-methylpyridinium-3-yl, 3-phenyl-N-methylpyridinium-3-yl or 4-phenyl-N-methylpyridinium-4-yl; and R4 is H, phenyl, pyridin-4-yl, methylpyridinium, N-methylpyridinium-3-yl; 2-phenyl-N-methylpyridinium-4-yl, 3-phenyl-N-methylpyridinium-4-yl, 4-phenyl-N-methylpyridinium-4-yl, 2-phenyl-N-methylpyridinium-3-yl, 3-phenyl-N-methylpyridinium-3-yl or 4-phenyl-N-methylpyridinium-4-yl;

and wherein any one or more of R1, R2, R3 and R4 may be optionally substituted.

In one embodiment of the first aspect, the PDC comprises any suitable molecular structure or chromophore activated or photochemically excited when exposed to light. The molecular structure or chromophore may absorb light, transfer energy, and produce cytotoxic oxygen species which can be used to treat cancer cells and other diseases. The molecular structure or chromophore may comprise any suitable scaffold which can accommodate R1, R2, R3 and R4. The molecular structure or chromophore may be covalently bound to one or more or each of R1, R2, R3 and R4. The PDC may comprise an hydrocarbyl or hetero-hydrocarbyl scaffold.

The PDC may absorb visible light between 420 and 520 nm.

The PDC may comprise a cyclic tetrapyrrole. The cyclic tetrapyrrole may comprise a porphin, a porphyrin, a chlorin or a corrin.

In one embodiment, the compound of formula (i) may be characterised by an absorption band at 620 to 700 nm. The absorption band may be at greater than 620 nm.

In one particular embodiment of the first aspect, the PDC comprises the compound of formula (I) wherein R1, R2, R3 and R4 comprise H.

In another embodiment of the first aspect, R1, R2, R3 and R4 are as defined in Table 1.

In yet another embodiment of the first aspect, the compound of formula (i) is not symmetric or is asymmetric.

In still another embodiment of the first aspect, any two or three neighbouring R groups may be identical. The R groups may comprise two pairs of neighbouring identical R groups.

In another embodiment of the first aspect, the compound is a compound of formula (i):
provided that each of R1 to R4 are not H;
provided that each of R1 to R4 are not phenyl;
provided that each of R1 to R4 are not N-methylpyridinium-4-yl;
provided that each of R1 to R4 are not N-methylpyridinium-3-yl;
provided that each of R1 to R4 are not 2-phenyl-N-methylpyridinium-4-yl;
provided that each of R1 to R4 are not 3-phenyl-N-methylpyridinium-4-yl;
provided that each of R1 to R4 are not 4-phenyl-N-methylpyridinium-4-yl;
provided that each of R1 to R4 are not 2-phenyl-N-methylpyridinium-3-yl;
provided that each of R1 to R4 are not 3-phenyl-N-methylpyridinium-3-yl;
provided that each of R1 to R4 are not 4-phenyl-N-methylpyridinium-3-yl; or
provided that R1 and R2 are not both N-methylpyridinium-4-yl and R3 and
R4 are not both H.

In another embodiment of the first aspect, the compound of formula (i) is positively charged.

In yet another embodiment of the first aspect, the compound of the formula (i) comprises far-infrared absorption spectroscopic properties to absorb far-infrared light penetrating through skin to tumour cells.

In still another embodiment of the first aspect, the compound of formula (i) may block Ras-Raf interaction.

In another embodiment of the first aspect, the compound of formula (i) may disrupt Ras-Raf dependent signalling.

In yet another embodiment of the first aspect, the compound of formula (i) may specifically target oncogenic Ras protein in human tumour cells.

In a second aspect, although it need not be the only or indeed the broadest aspect, the invention resides in a compound selected from the group consisting of compounds of formula (I), or a pharmaceutically acceptable salt thereof:

formula (I)

wherein

R1 is H, phenyl, pyridin-4-yl, methylpyridinium, N-methylpyridinium-3-yl; 2-phenyl-N-methylpyridinium-4-yl, 3-phenyl-N-methylpyridinium-4-yl, 4-phenyl-N-methylpyridinium-4-yl, 2-phenyl-N-methylpyridinium-3-yl, 3-phenyl-N-methylpyridinium-3-yl or 4-phenyl-N-methylpyridinium-3-yl;

R2 is H, phenyl, pyridin-4-yl, methylpyridinium, N-methylpyridinium-3-yl; 2-phenyl-N-methylpyridinium-4-yl, 3-phenyl-N-methylpyridinium-4-yl, 4-phenyl-N-methylpyridinium-4-yl, 2-phenyl-N-methylpyridinium-3-yl, 3-phenyl-N-methylpyridinium-3-yl or 4-phenyl-N-methylpyridinium-3-yl;

R3 is H, phenyl, pyridin-4-yl, methylpyridinium, N-methylpyridinium-3-yl; 2-phenyl-N-methylpyridinium-4-yl, 3-phenyl-N-methylpyridinium-4-yl, 4-phenyl-N-methylpyridinium-4-yl, 2-phenyl-N-methylpyridinium-3-yl, 3-phenyl-N-methylpyridinium-3-yl or 4-phenyl-N-methylpyridinium-3-yl; and R4 is H, phenyl, pyridin-4-yl, methylpyridinium, N-methylpyridinium-3-yl; 2-phenyl-N-methylpyridinium-4-yl, 3-phenyl-N-methylpyridinium-4-yl, 4-phenyl-N-methylpyridinium-4-yl, 2-phenyl-N-methylpyridinium-3-yl, 3-phenyl-N-methylpyridinium-3-yl or 4-phenyl-N-methylpyridinium-3-yl;

and
wherein any one or more of R1, R2, R3 and R4 may be optionally substituted.

In one embodiment of the second aspect, R1, R2, R3 and R4 are as defined in Table 1.

In another embodiment of the second aspect, the compound of formula (I) is not symmetric or is asymmetric.

In yet another embodiment of the second aspect, any two or three neighbouring R groups may be identical. The R groups may comprise two pairs of neighbouring identical R groups.

In still another embodiment of the second aspect, the compound is a compound of formula (I):
provided that each of R1 to R4 are not H;
provided that each of R1 to R4 are not phenyl;
provided that each of R1 to R4 are not N-methylpyridinium-4-yl;
provided that each of R1 to R4 are not N-methylpyridinium-3-yl;
provided that each of R1 to R4 are not 2-phenyl-N-methylpyridinium-4-yl;
provided that each of R1 to R4 are not 3-phenyl-N-methylpyridinium-4-yl;
provided that each of R1 to R4 are not 4-phenyl-N-methylpyridinium-4-yl;
provided that each of R1 to R4 are not 2-phenyl-N-methylpyridinium-3-yl;
provided that each of R1 to R4 are not 3-phenyl-N-methylpyridinium-3-yl;
provided that each of R1 to R4 are not 4-phenyl-N-methylpyridinium-3-yl; or
provided that R1 and R2 are not both N-methylpyridinium-4-yl and R3 and
R4 are not both H.

In another embodiment of the second aspect, the compound of formula (I) is positively charged.

In yet another embodiment of the second aspect, the compound of the formula (I) comprises far-infrared absorption spectroscopic properties to absorb far-infrared light penetrating through skin to tumour cells.

In still another embodiment of the second aspect, the compound of formula (I) may block Ras-Raf interaction.

In another embodiment of the second aspect, the compound of formula (I) may disrupt Ras-Raf dependent signalling.

In yet another embodiment of the second aspect, the compound of formula (I) may specifically target oncogenic Ras protein in human tumour cells.

According to a third aspect of the invention, there is provided a pharmaceutical composition comprising an effective amount of a compound of the first or second aspect, or a pharmaceutically acceptable salt thereof, and a pharmaceutically acceptable carrier, diluent and/or excipient.

Suitably, the pharmaceutical composition is for the treatment or prophylaxis of a cancer, or associated disease, disorder or condition.

A fourth aspect of the invention resides in a method of treating a cancer, or associated disease, disorder or condition in a patient including the step of administering an effective amount of a compound of the first or second aspect, or a pharmaceutically effective salt thereof, or the pharmaceutical composition of the third aspect to the patient, to thereby treat the cancer, or associated disease, disorder or condition.

The method of the fourth aspect may further comprise photo-activating the administered compound to release radical oxygen species with cytotoxcity.

The photoactivation may comprise long wavelength light. The long wavelength light may comprise a wavelength of between 600 and 850 nm. The long wavelength light may be at or greater than 620 nm. In particular embodiments, the photoactivation may comprise long wavelength light of a wavelength of about 660 nm and/or about 637 nm.

A fifth aspect of the invention provides for a compound of the first or second aspect, or a pharmaceutically effective salt thereof, or the pharmaceutical composition of the third aspect for use in the treatment of a cancer, or associated disease, disorder or condition.

A sixth aspect of the invention provides for use of a compound of the first aspect, or a pharmaceutically effective salt thereof, in the manufacture of a medicament for the treatment of a cancer, or associated disease, disorder or condition.

A seventh aspect of the invention provides a method of treating a cancer, or associated disease, disorder or condition in a patient including the step of administering an effective amount of a photosensitizer that is photoactivated by long wavelength light and activating the photosensitizer with long wavelength light. The long wavelength light may comprise a wavelength of between 600 and 850 nm. In particular embodiments, the photo-activation may comprise long wavelength light of a wavelength of about 660 nm and/or about 637 nm.

In one embodiment of the seventh aspect, the photosensitizer comprises the compound of the first or second aspect, or a pharmaceutically effective salt thereof, or the pharmaceutical composition of the third aspect.

In another embodiment of the seventh aspect, the cancer, or associated disease, disorder or condition treated is one that requires tissue penetration. The penetration may be up to 3 cm. The penetration may be up to 1 to 5 cm; 2 to 4 cm; or 2.5 to 3.5 cm. The penetration may be up to 1.0; 1.1; 1.2; 1.3; 1.4; 1.5; 1.6; 1.7; 1.8; 1.9; 2.0; 2.1; 2.2; 2.3; 2.4; 2.5; 2.6; 2.7; 2.8; 2.9; 3.0; 3.1; 3.2; 3.3; 3.4; 3.5; 3.6; 3.7; 3.8; 3.9; 4.0; 4.1; 4.2; 4.3; 4.4; 4.5; 4.6; 4.7; 4.8; 4.9 or 5.0 cm.

An eighth aspect of the invention provides a method of modulating one or more oncogenic protein and/or treating a cancer or an associated disease, disorder or condition comprising administering to a patient in need thereof one or more photodynamically active compound comprising one or more charged moiety to thereby modulate the one or more oncogenic protein and/or treat the cancer or associated disease, disorder or condition.

The modulation may comprise modulation of Ras. The modulation may comprise blocking Ras-Raf interaction. The modulation may disrupt Ras-Raf dependent signalling. The one or more charged moiety on the photodynamically active compound may specifically target oncogenic Ras protein in human tumour cells.

The photodynamically active compound may comprise a photodynamic core.

The one or more charged moiety on a photodynamically active compound may comprise the compound of formula (i) or (I) wherein R1, R2, R3 and R4 are H. The one or more charged moiety may comprise one or more of benzenephenyl, 4-pyridine-4-yl, 4-methylpyridinium, 3N-methylpyridinium-3-yl; 2-phenyl-4N-methylpyridinium-4-yl, 3-phenyl-4N-methylpyridinium-4-yl, 4-phenyl-4N-methylpyridinium-4-yl, 2-phenyl-3N-methylpyridinium-3-yl, 3-phenyl-3N-methylpyridinium-3-yl or 4-phenyl-3N-methylpyridinium-3-yl.

In one embodiment of the eighth aspect, the photodynamically active compound may be activated by long wavelength light. The photo-activation by long wavelength light may allow improved tissue penetration.

In one embodiment of the fourth, fifth, sixth or seventh aspects, the cancer, or associated disease, disorder or condition is one or more of a skin cancer, a lung cancer, a pancreatic cancer, a colon cancer, an ovarian cancer, an adenocarcinoma, a leukemia (AML), and a lymphoma.

Preferably, the patient is a companion or domestic, performance or livestock animal or a human.

The various features and embodiments of the present invention, referred to in individual sections above apply, as appropriate, to other sections, mutatis mutandis. Consequently features specified in one section may be combined with features specified in other sections as appropriate.

Further features and advantages of the present invention will become apparent from the following detailed description.

BRIEF DESCRIPTION OF THE DRAWINGS

In order that the invention may be readily understood and put into practical effect, reference will now be made to embodiments of the present invention with reference to the accompanying drawings, wherein like reference numbers refer to identical elements. The drawings are provided by way of example only, wherein.

Figure 1A:
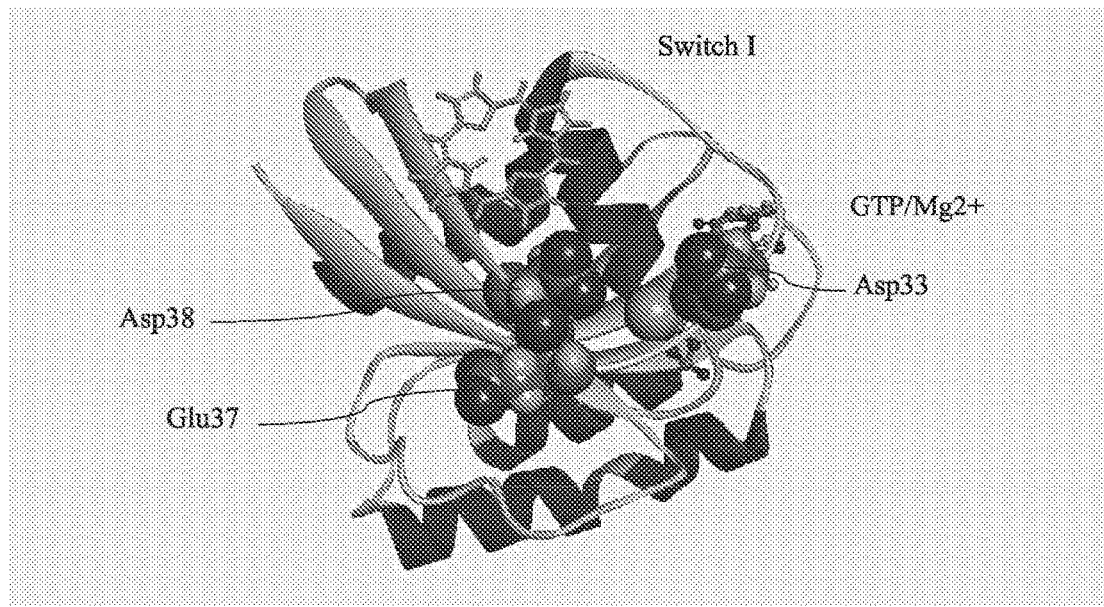
FIG. 1A is a ribbon diagram showing the three-dimensional structure of the Ras protein.

Skilled addressees will appreciate that elements in the figures are illustrated for simplicity and clarity and have not necessarily been entirely accurately.

DETAILED DESCRIPTION OF THE INVENTION

The present invention relates to compounds and methods for treatment of a cancer, or associated disease, disorder or condition. Advantageously, the compounds may comprise photodynamic activity and may be photodynamically activated to induce cytotoxicity.

The invention is at least partly predicated on the unexpected discovery of novel compounds for the treatment of a cancer, or associated disease, disorder or condition. A further unexpected discovery was that these compounds may comprise the photosensitizer in photodynamic therapy.

The invention may find application in the treatment of any suitable cancer, or associated disease, disorder or condition including for example, one or more of a skin cancer, a lung cancer, a pancreatic cancer, a colon cancer, an ovarian cancer, an adenocarcinoma, a leukemia (AML), and a lymphoma.

In one embodiment, the inventors have designed and developed a novel treatment of cancer diseases, disorders and conditions based on an approach which utilises novel compounds, targeting the oncogenic Ras protein and optionally photodynamic therapy. The inventors have discovered novel compounds that target Ras proteins and thereby block Ras-Raf interactions. The compounds may disrupt the Ras-Raf dependent signalling pathway involved in many cancer types. Additionally, the compounds specifically target oncogenic Ras proteins in human tumour cells. Further, the compounds may be used as the photosensitiser for Photodynamic Therapy (PDT).

The compounds of the invention are of particular advantage because they are of long wavelength absorption so as to absorb the far-infrared light that penetrates into the body. This increased tissue penetration means the compounds of the invention can be photo activated from photo-stimulus provided from outside the body yet still target cancers located in the lung, pancreas, colon, ovaries or of adenocarcinoma, leukemia and lymphoma type.

The overall scheme of mechanism may comprise two steps:

1) upon administration of one or more compound, it will locate the oncogenic Ras protein in tumour cells, and partially block the Ras-Raf dependent signalling pathway; and 2) using specific light, the one or more compound (photosensitiser) will be activated to generate radical oxygen species with cytotoxcity to kill the tumour, as is done in Photodynamic Therapy.

The photoactivation may comprise long wavelength light. The photoactivation may be by light comprising a wavelength between 600 nm and 850 nm. In particular embodiments, the long wavelength light may comprise a wavelength of about 660 nm and/or about 637 nm.

The compounds of the invention may be generalized as a new generation of photosensitizers comprising a photodynamic core (PDC) and functional groups R1, R2, R3 and R4. The PDC may be activated by photodynamic therapy when exposed to light. One or more of the functional groups (R1, R2, R3, R4) may specifically bind to the target protein involved in disease, which may be for example the oncogenic Ras protein which is involved in about 30% of tumour types.

In one embodiment, the invention resides in a compound selected from the group consisting of a compound of formula (i), or a pharmaceutically acceptable salt thereof:

formula (i)

wherein PDC is a photodynamic core; and wherein
R1 is H, phenyl, pyridin-4-yl, N-methylpyridinium-4-yl, N-methylpyridinium-3-yl, 2-phenyl-N-methylpyridinium-4-yl, 3-phenyl-N-methylpyridinium-4-yl, 4-phenyl-N-methylpyridinium-4-yl, 2-phenyl-N-methylpyridinium-3-yl, 3-phenyl-N-methylpyridinium-3-yl or 4-phenyl-N-methylpyridinium-3-yl;
R2 is H, phenyl, pyridin-4-yl, N-methylpyridinium-4-yl, N-methylpyridinium-3-yl, 2-phenyl-N-methylpyridinium-4-yl, 3-phenyl-N-methylpyridinium-4-yl, 4-phenyl-N-methylpyridinium-4-yl, 2-phenyl-N-methylpyridinium-3-yl, 3-phenyl-N-methylpyridinium-3-yl or 4-phenyl-N-methylpyridinium-3-yl;
R3 is H, phenyl, pyridin-4-yl, N-methylpyridinium-4-yl, N-methylpyridinium-3-yl, 2-phenyl-N-methylpyridinium-4-yl, 3-phenyl-N-methylpyridinium-4-yl, 4-phenyl-N-methylpyridinium-4-yl, 2-phenyl-N-methylpyridinium-3-yl, 3-phenyl-N-methylpyridinium-3-yl or 4-phenyl-N-methylpyridinium-3-yl; and
R4 is H, phenyl, pyridin-4-yl, N-methylpyridinium-4-yl, N-methylpyridinium-3-yl, 2-phenyl-N-methylpyridinium-4-yl, 3-phenyl-N-methylpyridinium-4-yl, 4-phenyl-N-methylpyridinium-4-yl, 2-phenyl-N-methylpyridinium-3-yl, 3-phenyl-N-methylpyridinium-3-yl or 4-phenyl-N-methylpyridinium-3-yl;
and
wherein any one or more of R1, R2, R3 and R4 may be optionally substituted.

The PDC may comprise any suitable molecular structure or chromophore activated or photochemically excited when exposed to light. The molecular structure or chromophore may comprise any suitable scaffold which may accommodate R1, R2, R3 and R4. The PDC may comprise a hydrocarbyl or heterohydrocarbyl scaffold.

The PDC may absorb visible light between 420 nm and 520 nm.

The PDC may comprise a cyclic tetrapyrrole. The cyclic tetrapyrrole may comprise a porphin, a porphyrin, a chlorin or a corrin.

In one embodiment, the compound of formula (i) may be characterised by an absorption band at 620 to 700 nm. The absorption band may be at or greater than 620 nm.

The PDC may comprise the compound of formula (I) wherein R1, R2, R3 and R4 comprise H. The compound of formula (i) may not be symmetrical or may be asymmetrical.

The compound of the invention may comprise a compound of formula (i):
provided that each of R1 to R4 are not H;
provided that each of R1 to R4 are not phenyl;
provided that each of R1 to R4 are not N-methylpyridinium-4-yl;
provided that each of R1 to R4 are not N-methylpyridinium-3-yl;
provided that each of R1 to R4 are not 2-phenyl-N-methylpyridinium-4-yl;
provided that each of R1 to R4 are not 3-phenyl-N-methylpyridinium-4-yl;
provided that each of R1 to R4 are not 4-phenyl-N-methylpyridinium-4-yl;
provided that each of R1 to R4 are not 2-phenyl-N-methylpyridinium-3-yl;
provided that each of R1 to R4 are not 3-phenyl-N-methylpyridinium-3-yl;
provided that each of R1 to R4 are not 4-phenyl-N-methylpyridinium-3-yl; or
provided that R1 and R2 are not both N-methylpyridinium-4-yl and R3 and R4 are not both H.

The compound of formula (i) may be positively charged. The compound of formula (i) may exhibit far-infrared absorption spectroscopic properties for absorbing far-infrared light penetrating through skin to tumour cells when present in a subject being treated with PDT. The compound of formula (i) may block Ras-Raf interaction. The compound of formula (i) may disrupt Ras-Raf dependent signalling. The compound of formula (i) may specifically target oncogenic Ras protein in human tumour cells.

In another embodiment, the compounds of the invention may be selected from the group consisting of compounds of formula (I), or a pharmaceutically acceptable salt thereof:

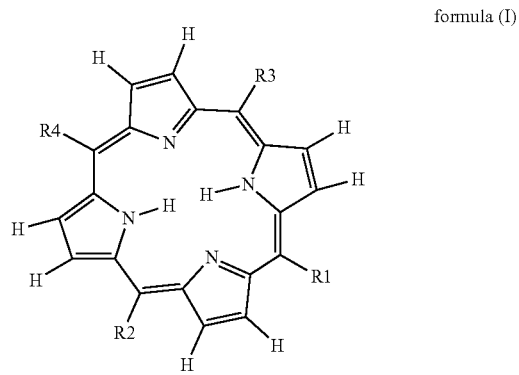

formula (I)

wherein
R1 is H, phenyl, pyridin-4-yl, methylpyridinium, N-methylpyridinium-3-yl, 2-phenyl-N-methylpyridinium-4-yl, 3-phenyl-N-methylpyridinium-4-yl, 4-phenyl-N-methylpyridinium-4-yl, 2-phenyl-N-methylpyridinium-3-yl, 3-phenyl-N-methylpyridinium-3-yl or 4-phenyl-N-methylpyridinium-3-yl;

R2 is H, phenyl, pyridin-4-yl, methylpyridinium, N-methylpyridinium-3-yl, 2-phenyl-N-methylpyridinium-4-yl, 3-phenyl-N-methylpyridinium-4-yl, 4-phenyl-N-methylpyridinium-4-yl, 2-phenyl-N-methylpyridinium-3-yl, 3-phenyl-N-methylpyridinium-3-yl or 4-phenyl-N-methylpyridinium-3-yl;

R3 is H, phenyl, pyridin-4-yl, methylpyridinium, N-methylpyridinium-3-yl, 2-phenyl-N-methylpyridinium-4-yl, 3-phenyl-N-methylpyridinium-4-yl, 4-phenyl-N-methylpyridinium-4-yl, 2-phenyl-N-methylpyridinium-3-yl, 3-phenyl-N-methylpyridinium-3-yl or 4-phenyl-N-methylpyridinium-3-yl; and R4 is H, phenyl, pyridin-4-yl, methylpyridinium, N-methylpyridinium-3-yl, 2-phenyl-N-methylpyridinium-4-yl, 3-phenyl-N-methylpyridinium-4-yl, 4-phenyl-N-methylpyridinium-4-yl, 2-phenyl-N-methylpyridinium-3-yl, 3-phenyl-N-methylpyridinium-3-yl or 4-phenyl-N-methylpyridinium-3-yl.

Importantly, one or more of R1, R2, R3 and R4 may be optionally substituted, in accordance with the example substitution discussed below.

In certain embodiments, the compound of formula (I) is as above, with one or more of the following provisos:
provided that each of R1 to R4 are not H;
provided that each of R1 to R4 are not phenyl;
provided that each of R1 to R4 are not N-methylpyridinium-4-yl;
provided that each of R1 to R4 are not N-methylpyridinium-3-yl;
provided that each of R1 to R4 are not 2-phenyl-N-methylpyridinium-4-yl;
provided that each of R1 to R4 are not 3-phenyl-N-methylpyridinium-4-yl;
provided that each of R1 to R4 are not 4-phenyl-N-methylpyridinium-4-yl;
provided that each of R1 to R4 are not 2-phenyl-N-methylpyridinium-3-yl;
provided that each of R1 to R4 are not 3-phenyl-N-methylpyridinium-3-yl;
provided that each of R1 to R4 are not 4-phenyl-N-methylpyridinium-3-yl; and
provided that R1 and R2 are not both N-methylpyridinium-4-yl and R3 and R4 are not both H.

Examples of R1, R2, R3 and R4 for both compounds (i) and (I) are provided Table 1.

In a particular embodiment, the compound of formula (I) may not be symmetric, or put another way, may be asymmetric. Any two or three neighbouring R groups may be identical. The R groups may comprise two pairs of neighbouring identical R groups.

In one embodiment, the compound of formula (I) is not the compound wherein R1 and R2 are N-methylpyridinium-4-yl and R3 and R4 are both H.

In a particular embodiment, the compound of formula (I) is positively charged.

As used herein, "effective amount" refers to the administration of an amount of the relevant active agent sufficient to prevent the occurrence of symptoms of the cancer, disease, disorder or condition being treated, or to bring about a halt in the worsening of symptoms or to treat and alleviate or at least reduce the severity of the symptoms. The effective amount will vary in a manner which would be understood by a person of skill in the art with patient age, sex, weight, etc being just a sample of factors to be considered. An appropriate dosage or dosage regime can be ascertained through routine trials.

The term "pharmaceutically acceptable salt", as used herein, refers to salts which are toxicologically safe for systemic or localised administration such as salts prepared from pharmaceutically acceptable non-toxic bases or acids including inorganic or organic bases and inorganic or organic acids. The pharmaceutically acceptable salts may be selected from the group including alkali and alkali earth, ammonium, aluminium, iron, amine, glucosamine, halide such as chloride, sulphate, sulphonate, bisulphate, nitrate, citrate, tartrate, bitarate, phosphate, carbonate, bicarbonate, malate, maleate, napsylate, fumarate, succinate, acetate, benzoate, terephthalate, palmoate, piperazine, pectinate and S-methyl methionine salts and the like.

"Substituted" or "Optionally substituted" in reference to a substituent group refers to substituent groups optionally substituted with one or more moieties, for example, those selected from the group consisting of optionally substituted $C_{1-10}$ alkyl (e.g., optionally substituted $C_{1-6}$ alkyl); optionally substituted $C_{1-10}$ alkoxy (e.g., optionally substituted $C_{1-6}$ alkoxy); optionally substituted $C_{2-10}$ alkenyl; optionally substituted $C_{2-10}$ alkynyl; optionally substituted $C_6$-$C_{12}$ aryl; aryloxy; optionally substituted heteroaryl; optionally substituted heterocycle; halo (e.g., Cl, F, Br, and I); hydroxyl; halogenated alkyl (e.g., $CF_3$, 2-Br-ethyl, $CH_2F$, $CF_2H$, $CH_2CF_3$, and $CF_2CF_3$); amino (e.g., $NH_2$, NR12H, and NR12R13); alkylamino; arylamino; acyl; amido; CN; $NO_2$; $N_3$; $CH_2OH$; $CONH_2$; CONR12R13; $CO_2R12$; $CH_2OR12$; NHCOR12; $NHCO_2R12$; $C_{1-3}$ alkylthio; sulfonyl, sulphonamide, sulfate; sulfonic acid; sulfonate esters such as alkyl or aralkyl sulfonyl, including methanesulfonyl; phosphonic acid; phosphate; and phosphonate, wherein R12 and R13 are each independently selected from H or optionally substituted $C_{1-10}$ alkyl.

The term "alkyl" refers to a straight-chain or branched alkyl substituent containing from, for example, 1 to about 12 carbon atoms, preferably 1 to about 9 carbon atoms, more preferably 1 to about 6 carbon atoms, even more preferably from 1 to about 4 carbon atoms, still yet more preferably from 1 to 2 carbon atoms. Examples of such substituents may be selected from the group consisting of methyl, ethyl, propyl, isopropyl, n-butyl, sec-butyl, isobutyl, tert-butyl, pentyl, isoamyl, 2-methylbutyl, 3-methylbutyl, hexyl, heptyl, 2-methylpentyl, 3-methylpentyl, 4-methylpentyl, 2-ethylbutyl, 3-ethylbutyl, octyl, nonyl, decyl, undecyl, dodecyl and the like. The number of carbons referred to relates to the carbon backbone and carbon branching but does not include carbon atoms belonging to any substituents that may optionally be present, for example the carbon atoms of an alkoxy substituent branching off the main carbon chain. Substituted alkyl includes alkyl substituted with one or more moieties selected from the group consisting of halo (e.g., Cl, F, Br, and I); halogenated alkyl (e.g., $CF_3$, 2-Br-ethyl, $CH_2F$, $CF_2H$, $CH_2Cl$, $CH_2CF_3$, or $CF_2CF_3$); hydroxyl; amino; carboxylate; carboxamido; alkylamino; arylamino; alkoxy; aryloxy; nitro; azido; cyano; thio; sulfonyl, sulphonamide, sulfonic acid; sulfate; phosphonic acid; phosphate; and phosphonate.

The term "alkenyl" refers to optionally substituted unsaturated linear or branched hydrocarbon groups, having 2 to 12 carbon atoms, preferably 2 to 9 carbon atoms, more preferably 2 to 6 carbon atoms and having at least one carbon-carbon double bond. Where appropriate, the alkenyl group may have a specified number of carbon atoms, for example, C2-C6 alkenyl which includes alkenyl groups having 2, 3, 4, 5 or 6 carbon atoms in linear or branched arrangements. The number of carbons referred to relates to the carbon backbone and carbon branching but does not include carbon atoms belonging to any substituents that may optionally be present. Examples of such substituents may be selected from the group consisting of ethenyl, propenyl, isopropenyl, butenyl, s- and t-butenyl, pentenyl, hexenyl, hept-1,3-diene, hex-1,3-diene, non-1,3,5-triene and the like. Substituted alkyl includes alkyl substituted with one or more moieties selected from the group consisting of halo (e.g., Cl, F, Br, and I); halogenated alkyl (e.g., $CF_3$, 2-Br-ethyl, $CH_2F$, $CF_2H$, $CH_2Cl$, $CH_2CF_3$, or $CF_2CF_3$); hydroxyl; amino; carboxylate; carboxamido; alkylamino; arylamino; alkoxy; aryloxy; nitro; azido; cyano; thio; sulfonyl, sulphonamide, sulfonic acid; sulfate; phosphonic acid; phosphate; and phosphonate.

The term "carboalkoxy" refers to an alkyl ester of a carboxylic acid, wherein alkyl has the same definition as found above. Examples include carbomethoxy, carboethoxy, carboisopropoxy and the like.

The term "alkoxy" as used herein means straight or branched chain alkyl groups linked by an oxygen atom (i.e., —O-alkyl), wherein alkyl is as described above. In particular embodiments, alkoxy refers to oxygen-linked groups comprising 1 to 10 carbon atoms ("C1-10 alkoxy"). In further embodiments, alkoxy refers to oxygen-linked groups comprising 1 to 8 carbon atoms ("C1-8 alkoxy"), 1 to 6 carbon atoms ("C1-6 alkoxy"), 1 to 4 carbon atoms ("C1-4 alkoxy") or 1 to 3 carbon atoms ("C1-3 alkoxy").

The terms "cycloalkyl" and "cycloalkenyl" refers to optionally substituted saturated and unsaturated mono-cyclic, bicyclic or tricyclic carbon groups. Where appropriate, the cycloalkyl or cycloalkenyl group may have a specified number of carbon atoms, for example, C3-C6 cycloalkyl or cycloalkenyl includes within its scope a carbocyclic group having 3, 4, 5 or 6 carbon atoms. C4-C7 cycloalkyl or cycloalkenyl may be preferred in certain embodiments. C5-C6 cycloalkyl or cycloalkenyl may be preferred in certain embodiments. Examples of such substituents may be selected from the group consisting of cyclopropyl, cyclobutyl, cyclopentyl, cyclopentenyl, cyclohexyl, cyclohexenyl, cyclohexadienyl and the like. Substituted cycloalkyl or cycloalkenyl includes substitutions with one or more moieties selected from the group consisting of halo (e.g., Cl, F, Br, and I); halogenated alkyl (e.g., $CF_3$, 2-Br-ethyl, $CH_2F$, $CH_2Cl$, $CH_2CF_3$, or $CF_2CF_3$); hydroxyl; sulfonyl, sulphonamide, amino; carboxylate; carboxamido; alkylamino; arylamino; alkoxy; aryloxy; nitro; azido; cyano; thio; sulfonic acid; sulfate; phosphonic acid; phosphate; and phosphonate.

The term "phenyl" or "aryl" refers to an unsubstituted or substituted aromatic carbocyclic substituent, as commonly understood in the art. It is understood that the term phenyl or aryl applies to cyclic substituents that are planar and comprise 4n+2 π electrons, according to Huckel's Rule.

The term "heteroaryl" refers to an aryl group containing from one or more (particularly one to four) non-carbon atom(s) (particularly N, O or S) or a combination thereof, which heteroaryl group is optionally substituted at one or more carbon or nitrogen atom(s). It may be a 4, 5, 6 or 7-membered ring, preferably 5 or 6-membered. Heteroaryl rings may also be fused with one or more cyclic hydrocarbon, heterocyclic, aryl, or heteroaryl rings. Heteroaryl includes, but is not limited to, 5-membered heteroaryls having one hetero atom (e.g., thiophenes, pyrroles, furans); 5 membered heteroaryls having two heteroatoms in 1, 2 or 1, 3 positions (e.g., oxazoles, pyrazoles, imidazoles, thiazoles, purines); 5-membered heteroaryls having three heteroatoms (e.g., triazoles, thiadiazoles); 5-membered heteroaryls having 3 heteroatoms; 6-membered heteroaryls with one heteroatom (e.g., pyridine, quinoline, isoquinoline, phenanthrine, 5,6-cycloheptenopyridine); 6-membered heteroaryls with two heteroatoms (e.g., pyridazines, cinnolines, phthalazines, pyrazines, pyrimidines, quinazolines); 6-membered heretoaryls with three heteroatoms (e.g. 1,3,5-triazine); and 6-membered heteroaryls with four heteroatoms. "Substituted heteroaryl" means a heteroaryl having one or more substituents.

"Heterocyclyl" as used herein specifically in relation to certain 'R' groups refers to a non-aromatic ring having 5 to 7 atoms in the ring and of those atoms 1 to 4 are heteroatoms, said ring being isolated or fused to a second ring wherein said heteroatoms are independently selected from O, N and S. 5 to 6 ring atoms may be preferred. Heterocyclic includes partially and fully saturated heterocyclic groups. Heterocyclic systems may be attached to another moiety via any number of carbon atoms or heteroatoms and may be both saturated and unsaturated. Non-limiting examples of heterocyclic groups include pyrrolidinyl, pyrrolinyl, pyranyl, piperidinyl, piperazinyl, morpholinyl, tetrahydrofuranyl, tetrahydrothiophenyl, pyrazolinyl, dithiolyl, oxathiolyl, dioxanyl, dioxinyl, oxazinyl, azepinyl, diazepinyl, thiazepinyl, oxepinyl and thiapinyl, imidazolinyl, thiomorpholinyl, and the like.

Whenever a range of the number of atoms in a structure is indicated (e.g., a $C_1$-$C_{12}$, $C_1$-$C_{10}$, $C_1$-$C_9$, $C_1$-$C_6$, $C_1$-$C_4$, or $C_2$-$C_{20}$, $C_2$-$C_{12}$, $C_2$-$C_{10}$, $C_2$-$C_9$, $C_2$-$C_8$, $C_2$-$C_6$, $C_2$-$C_4$ alkyl, alkenyl, etc.), it is specifically contemplated that any sub-range or individual number of carbon atoms falling within the indicated range can also be used. Thus, for instance, the recitation of a range of 1-12 carbon atoms (e.g., $C_1$-$C_{12}$), 1-9 carbon atoms (e.g., $C_1$-$C_9$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-8 carbon atoms (e.g., $C_2$-$C_8$) as used with respect to any chemical group (e.g., alkyl, etc.) referenced herein encompasses and specifically describes 1, 2, 3, 4, 5, 6, 7, 8, 9, 10, 11, and/or 12 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, and/or 4-12 carbon atoms, etc., as appropriate).

As used herein, the terms "subject" or "individual" or "patient" may refer to any subject, particularly a vertebrate subject, and even more particularly a mammalian subject, for whom therapy is desired. Suitable vertebrate animals include, but are not restricted to, primates, avians, livestock animals (e.g., sheep, cows, horses, donkeys, pigs), laboratory test animals (e.g., rabbits, mice, rats, guinea pigs, hamsters), companion animals (e.g., cats, dogs), performance animals (horses and dogs) and captive wild animals (e.g., foxes, deer, dingoes). A preferred subject is a human in need of treatment for a cancer, or associated disease, disorder or condition. However, it will be understood that the aforementioned terms do not imply that symptoms are necessarily present.

The compounds can be synthesised by approaches which are known in the art. Such approaches can be found in reference texts and journal articles including the following: Eriiks, J.; Vandergoot, H.; Sterk, G.; Timmerman, H. J. Med. Chem, 1992, 35, 3239-3246; Walczynski, K.; Timmerman, H.; Zuiderveld, O.; Zhang, M.; Glinka, R. II Farmaco, 1999, 54, 533-541; Ahangar, N.; Ayatti, A.; Alipour, E.; Pashapour, A.; Formadi, A.; Emmami, S. Chem Biol Drug Des. 2011, 78, 844-852; Caddick. S.; Judd. D.; Lewis. A.; Reich. M.; Williams.; M. Tetrahedron, 2003, 59, 5417-5423; Han, M.; Nam, K.; Shin, D.; Jeong, N.; Hahn, H. J. Comb. Chem.; 2010, 12, 518-530; Song, H; Wang, W.; Qin, Y. Synthetic Communications, 2005, 35, 2735-2748; and Duspara, P. A., et al. JOCS. 2012. 77, 10362-10368. Examples of synthetic approaches are included in the Examples below.

According to a third aspect of the invention there is provided a pharmaceutical composition comprising an effective amount of a compound of the first aspect, or a pharmaceutically acceptable salt thereof, and a pharmaceutically acceptable carrier, diluent and/or excipient.

Suitably, the pharmaceutical composition is for the treatment or prophylaxis of a cancer, or associated disease, disorder or condition.

The pharmaceutical composition may include more than one compound of the first or second aspect. When the composition includes more than one compound then the compounds may be in any ratio. The composition may further comprise known co-actives, delivery vehicles or adjuvants.

The compound of the first or second aspect is present in the pharmaceutical composition in an amount sufficient to inhibit or ameliorate the disease, disorder or condition which is the subject of treatment. Suitable dosage forms and rates of the compounds and the pharmaceutical compositions containing such may be readily determined by those skilled in the art.

Dosage forms may include tablets, dispersions, suspensions, injections, solutions, syrups, troches, capsules, suppositories, aerosols, transdermal patches and the like. These dosage forms may also include injecting or implanting devices designed specifically for, or modified to, ensure placement at the site of connective tissue degradation. A hydrogel is a preferred delivery form.

A fourth aspect of the invention resides in a method of treating a cancer, or associated disease, disorder or condition in a patient including the step of administering an effective amount of a compound of the first or second aspect, or a pharmaceutically effective salt thereof, or the pharmaceutical composition of the third aspect to the patient, to thereby treat the disease, disorder or condition.

A fifth aspect of the invention provides for a compound of the first or second aspect, or a pharmaceutically effective salt thereof, or the pharmaceutical composition of the third aspect for use in the treatment of a cancer, or associated disease, disorder or condition.

A sixth aspect of the invention provides for use of a compound of the first or second aspects, or a pharmaceutically effective salt thereof, in the manufacture of a medicament for the treatment of a cancer, or associated disease, disorder or condition.

A seventh aspect of the invention is a method of treating a cancer, or associated disease, disorder or condition in a patient including the step of administering an effective amount of a photosensitizer that is photoactivated by long wavelength light and activating the photosensitizer with long wavelength light. The long wavelength light may comprise a wavelength of between 600 and 850 nm. In particular embodiments, the photo-activation may comprise long wavelength light of a wavelength of about 660 nm and/or about 637 nm.

In one embodiment of the seventh aspect, the photosensitizer may comprise the compound of formula (i) or formula (I), or a pharmaceutically effective salt thereof, or the pharmaceutical composition of the third aspect.

Figure 11:
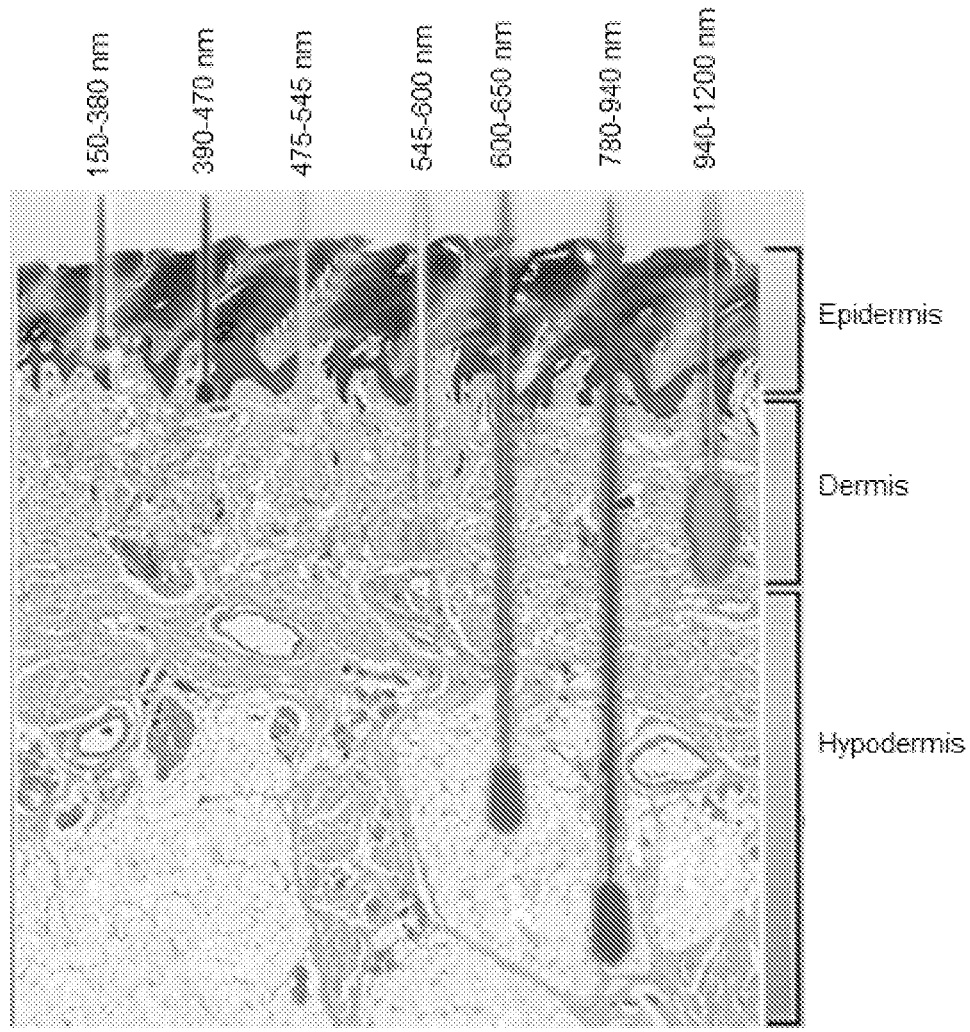
FIG. 11 is from Avci P, Guta A, et al., Low-Level Laser (Light) Therapy (LLLT) in Skin: Stimulating, Healing, Restoring (2013) Seminars in Cutaneous Medicine and Surgery, 32(1):41-52.

FIG. 11 is a figure taken from the prior art showing typical tissue penetration of various wavelengths of light.

In another embodiment of the seventh aspect, the cancer, or associated disease, disorder or condition treated is one that requires tissue penetration. The penetration may be up to 1 to 5 cm; 2 to 4 cm; or 2.5 to 3.5 cm. The penetration may be up to 1.0; 1.1; 1.2; 1.3; 1.4; 1.5; 1.6; 1.7; 1.8; 1.9; 2.0; 2.1; 2.2; 2.3; 2.4; 2.5; 2.6; 2.7; 2.8; 2.9; 3.0; 3.1; 3.2; 3.3; 3.4; 3.5; 3.6; 3.7; 3.8; 3.9; 4.0; 4.1; 4.2; 4.3; 4.4; 4.5; 4.6; 4.7; 4.8; 4.9 or 5.0 cm.

The patient may be a companion or domestic animal, livestock animal, performance animal or a human.

In one embodiment of the fourth, fifth or sixth aspects, the compound of the first or second aspect may be selected from any one or more compounds in Table 1 or any compound disclosed herein by way of a generic structure or exact chemical structure.

Dosage form and rates for pharmaceutical use and compositions are readily determinable by a person of skill in the art.

These dosage forms may also include injecting or implanting devices designed specifically for, or modified to, controlled release of the pharmaceutical composition.

Controlled release of the therapeutic agent may be effected by coating the same, for example, with hydrophobic polymers including acrylic resins, waxes, higher aliphatic alcohols, polylactic and polyglycolic acids and certain cellulose derivates such as hydroxypropylmethyl cellulose. In addition, the controlled release may be affected by using other polymer matrices, liposomes and/or microspheres.

Pharmaceutically acceptable carriers for systemic administration may also be incorporated into the compositions of the invention.

Suitably, the pharmaceutical composition comprises a pharmaceutically acceptable excipient. By "pharmaceutically acceptable excipient" is meant a solid or liquid filler, diluent or encapsulating substance that may be safely used in systemic administration. Depending upon the particular route of administration, a variety of carriers, well known in the art may be used. These carriers or excipients may be selected from a group including sugars, starches, cellulose and its derivatives, malt, gelatine, talc, calcium sulphate, vegetable oils, synthetic oils, polyols, alginic acid, phosphate buffered solutions, emulsifiers, isotonic saline, and pyrogen-free water.

Any suitable route of administration may be employed for providing a patient with the pharmaceutical composition of the invention. For example, oral including sublingual and buccal, rectal, parenteral including intravenous, intraarticular, intra-muscular, subcutaneous, intraperitoneal, intracerebroventricular, intra-dermal, inhalational, intraocular, transdermal and the like may be employed.

Pharmaceutical compositions of the invention suitable for administration may be presented in discrete units such as vials, capsules, sachets or tablets each containing a predetermined amount of one or more pharmaceutically active compounds of the invention, as a powder or granules or as a solution or a suspension in an aqueous liquid, a non-aqueous liquid, an oil-in-water emulsion or a water-in-oil emulsion. Such compositions may be prepared by any of the method of pharmacy but all methods include the step of bringing into association one or more pharmaceutically active compounds of the invention with the carrier which constitutes one or more necessary ingredients. In general, the compositions are prepared by uniformly and intimately admixing the agents of the invention with liquid carriers or finely divided solid carriers or both, and then, if necessary, shaping the product into the desired presentation.

In powders, the carrier is a finely divided solid which is in a mixture with the finely divided pharmaceutically active compound of the invention.

In tablets, the pharmaceutically active compound of the invention is mixed with the carrier having the necessary binding capacity in suitable proportions and compacted in the shape and size desired. The powders and tablets preferably contain from five or ten to about seventy percent of the pharmaceutically active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like.

The term "preparation" is intended to include the formulation of the pharmaceutically active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as admixture of fatty acid glycerides or cocoa butter, is first melted and the active component is dispersed homogeneously therein, for example by stirring. The molten homogenous mixture is then poured into convenient sized molds, allowed to cool, and thereby to solidify.

Liquid form preparations include solutions, suspensions, and emulsions, for example, water or water-propylene glycol solutions. For example, intravenous injection liquid preparations can be formulated as solutions in aqueous polyethylene glycol solution.

The compounds according to the present invention may thus be formulated for parenteral administration (e.g. by injection, for example bolus injection or continuous infusion) and may be presented in unit dose form in ampoules, pre-filled syringes, small volume infusion or in multidose containers with an added preservative. The compositions may take such forms as suspensions, solutions, or emulsions in oily or aqueous vehicles, and may contain formulatory agents such as suspending, stabilising and/or dispersing agents. Alternatively, the pharmaceutically active compound may be in powder form, obtained by aseptic isolation of sterile solid or by lyophilisation from solution, for constitution with a suitable vehicle, e.g. sterile, pyrogen-free water, before use.

Aqueous solutions suitable for oral use can be prepared by dissolving the pharmaceutically active compound in water and adding suitable colourants, flavours, stabilising and thickening agents, as desired.

Aqueous suspensions suitable for oral use can be made by dispersing the finely divided active compound in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilising agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising the pharmaceutically active compound in a flavoured base, usually sucrose and acacia or tragacanth; pastilles comprising the pharmaceutically active compound in an inert base such as gelatin and glycerin or sucrose and acacia; and mouthwashes comprising the pharmaceutically active compound in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomising spray pump. To improve nasal delivery and retention the compounds according to the invention may be encapsulated with cyclodextrins, or formulated with their agents expected to enhance delivery and retention in the nasal mucosa.

Administration to the respiratory tract may also be achieved by means of an aerosol formulation in which the active ingredient is provided in a pressurised pack with a suitable propellant such as a chlorofluorocarbon (CFC) for example, dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively, the pharmaceutically active compounds may be provided in the form of a dry powder, for example a powder mix of the compound in a suitable powder base such as lactose, starch, starch derivatives such as hydroxypropylmethyl cellulose and polyvinylpyrrolidone (PVP). Conveniently, the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the pharmaceutically active compound will generally have a small particle size for example of the order of 1 to 10 microns or less. Such a particle size may be obtained by means known in the art, for example by micronization.

So that the invention may be readily understood and put into practical effect, the following non-limiting Examples are provided.

EXAMPLES

Figure 1B:
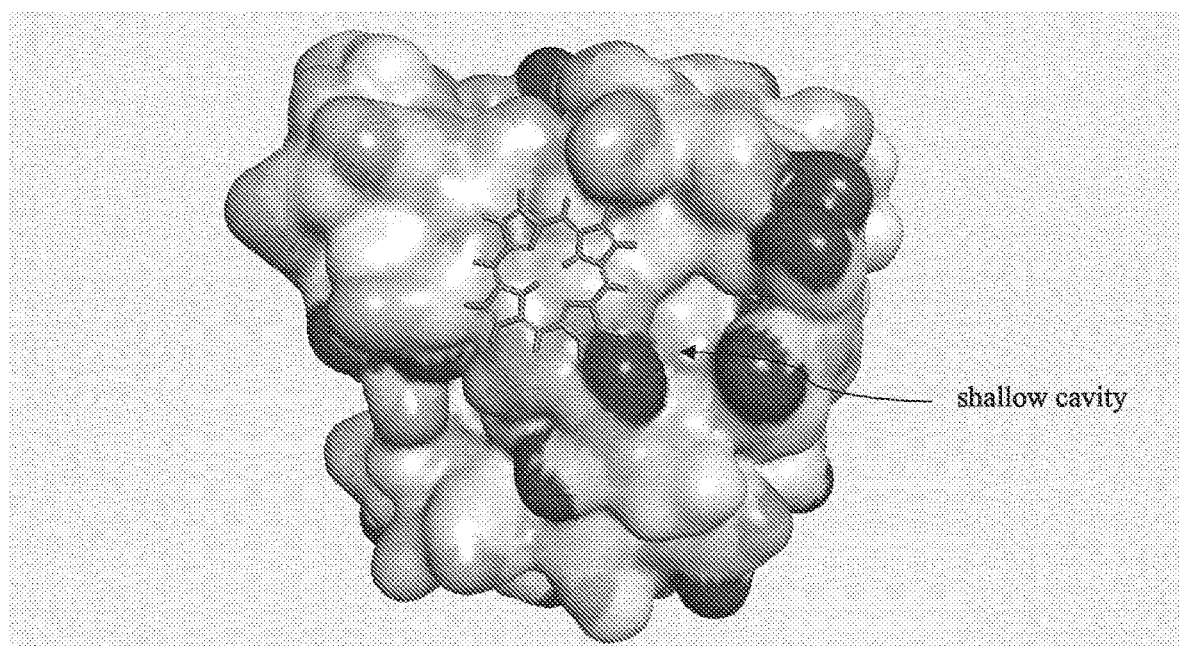
FIG. 1B is a space filling diagram showing the three-dimensional structure of the Ras protein.

1. Material and Methods 1.1 Chemical Scaffold on Ras protein: Porphyrin may be used as a scaffold for PSs due to its low toxicity and good photophysical and photochemical properties for Photodynamic Therapy. There are many crystal and NMR structures of Ras protein and Ras-RBD complexes available. The structure of Ras is taken from the crystal structure of the complex (3KUD). Multiple Copy Simultaneous Search Method "MCSS" (Caflisch A, Karplus M., J Comput.-Aided Mol. Des. 1996, 10:372, Zeng J. Comb. Chem. High Throughput Screen. 3:355) was used to map the best location of the scaffold (porphyrin) on Ras. This is where the scaffold binds to Ras protein with the strongest interaction energies. This binding structure was used as the template for the design of compounds with improved binding and spectroscopic properties. The most suitable porphyrin binding site on Switch I of Ras is shown with three charged residues (Asp33, Glu37 and Asp38) highlighted in space (FIG. 1). These residues in fact are located around a shallow cavity on the surface of the Switch I region of Ras protein, as illustrated in FIG. 1.

Figure 2:
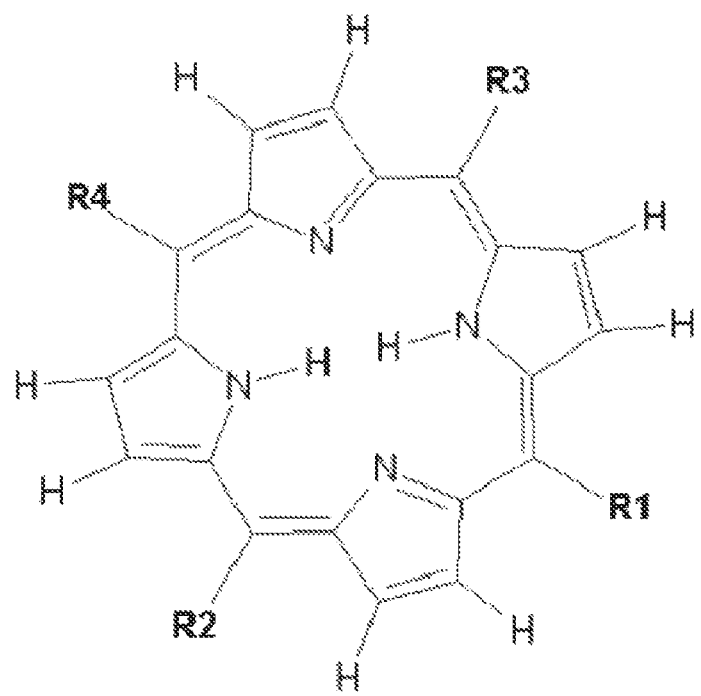
FIG. 2 shows the photodynamic core structure according to one embodiment of the invention. According to embodiments of the invention R1 is H, phenyl, pyridin-4-yl, N-methylpyridinium-4-yl, N-methylpyridinium-3-yl, 2-phenyl-N-methylpyridinium-4-yl, 3-phenyl-N-methylpyridinium-4-yl, 4-phenyl-N-methylpyridinium-4-yl, 2-phenyl-N-methylpyridinium-3-yl, 3-phenyl-N-methylpyridinium-3-yl or 4-phenyl-N-methylpyridinium-3-yl; R2 is H, phenyl, pyridin-4-yl, N-methylpyridinium-4-yl, N-methylpyridinium-3-yl, 2-phenyl-N-methylpyridinium-4-yl, 3-phenyl-N-methylpyridinium-4-yl, 4-phenyl-N-methylpyridinium-4-yl, 2-phenyl-N-methylpyridinium-3-yl, 3-phenyl-N-methylpyridinium-3-yl or 4-phenyl-N-methylpyridinium-3-yl; R3 is H, phenyl, pyridin-4-yl, N-methylpyridinium-4-yl, N-methylpyridinium-3-yl, 2-phenyl-N-methylpyridinium-4-yl, 3-phenyl-N-methylpyridinium-4-yl, 4-phenyl-N-methylpyridinium-4-yl, 2-phenyl-N-methylpyridinium-3-yl, 3-phenyl-N-methylpyridinium-3-yl or 4-phenyl-N-methylpyridinium-3-yl; and R4 is H, phenyl, pyridin-4-yl, N-methylpyridinium-4-yl, N-methylpyridinium-3-yl, 2-phenyl-N-methylpyridinium-4-yl, 3-phenyl-N-methylpyridinium-4-yl, 4-phenyl-N-methylpyridinium-4-yl, 2-phenyl-N-methylpyridinium-3-yl, 3-phenyl-N-methylpyridinium-3-yl or 4-phenyl-N-methylpyridinium-3-yl.

1.2 Design of compounds: Based on the scaffold and the nearby important residues of Ras protein, a series of compounds with R1 to R4 groups were designed to be able to form electrostatic interactions to the charged residues of the Switch I region of Ras protein (FIG. 1), and listed in Table 1 (also illustrated in FIG. 2). The compounds are positively charged in order to possess far-infrared absorption spectroscopic properties to absorb the far-infrared light which can penetrate through the skin to the tumour cells inside the body.

1.3 Synthesis of Representative Compounds: Two compounds from the Series I and II sets of compounds were selected as representative examples and synthesised. Series I and II Compounds are illustrated in FIG. 3. The Series I Compounds and Series II Compounds differ by virtue of the charged groups of R1-R4. Series I Compounds have two charged groups while Series II Compounds have only one charged group. In addition, the synthetic routes are different between Series 1 Compounds and Series two compounds.

Figure 3A:
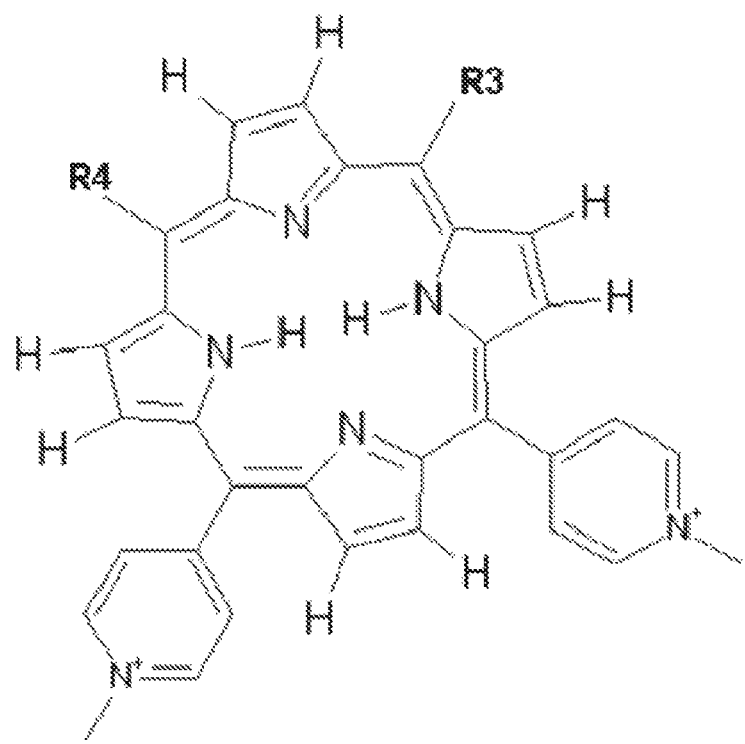
FIG. 3A shows the generic structure of the Series I compounds wherein R3 is H, or phenyl and R4=H or phenyl.

1.3.1 Representative Compound 4: comprised within Series I, wherein R3 and R4=H (see FIG. 3A). Synthesis of Representative Compound 4 was carried out by Synthesis Med Chem (Australia). The synthetic route is described in 1.6 below. The structure of Representative Compound 4 is shown in FIG. 3C.

Figure 3B:
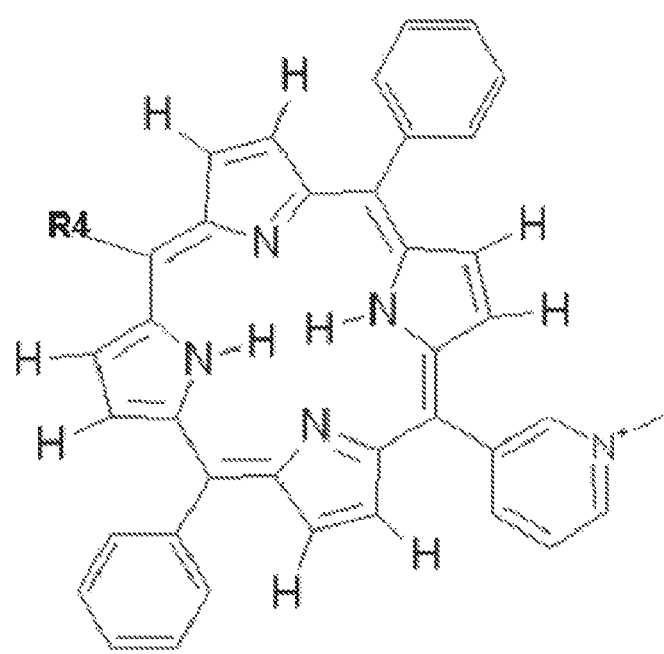
FIG. 3B shows the generic structure of the Series II compounds wherein R4 is H or phenyl.
Figure 3C:
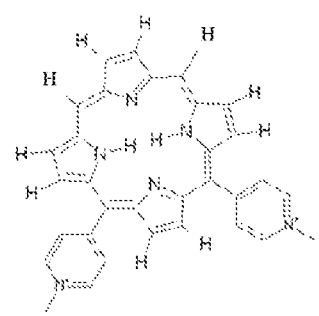
FIG. 3C shows the structure of Representative Compound 4.
Figure 3D:
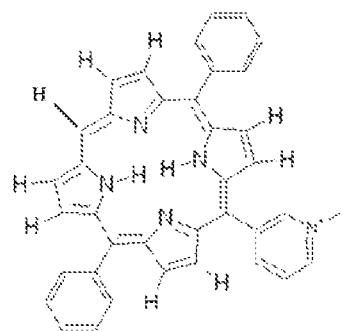
FIG. 3D shows the structure of Representative Compound 10.

1.3.2 Representative Compound 10: comprised within Series II wherein R3 and R4=phenyl (FIG. 3B). Synthesis of Representative Compound 10 was performed by Jubilant CHEMSYS (India). The synthetic route is described in 1.7 below. The structure of Representative Compound 10 is shown in FIG. 3D.

Figure 4A:
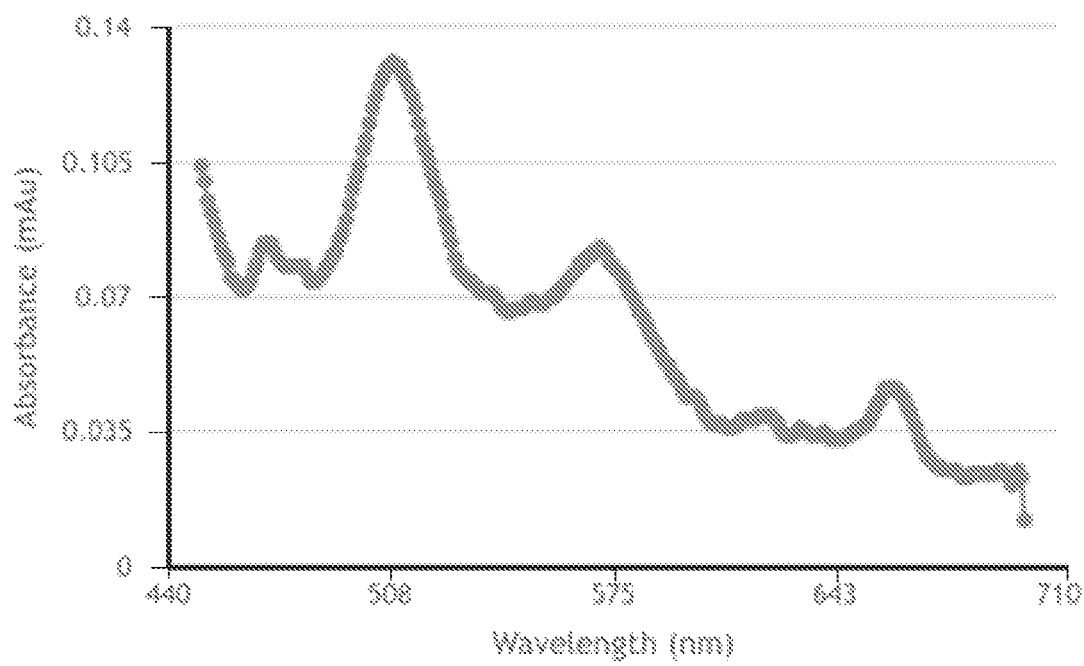
FIG. 4A shows the absorption spectra of Representative Compound 4.
Figure 4B:
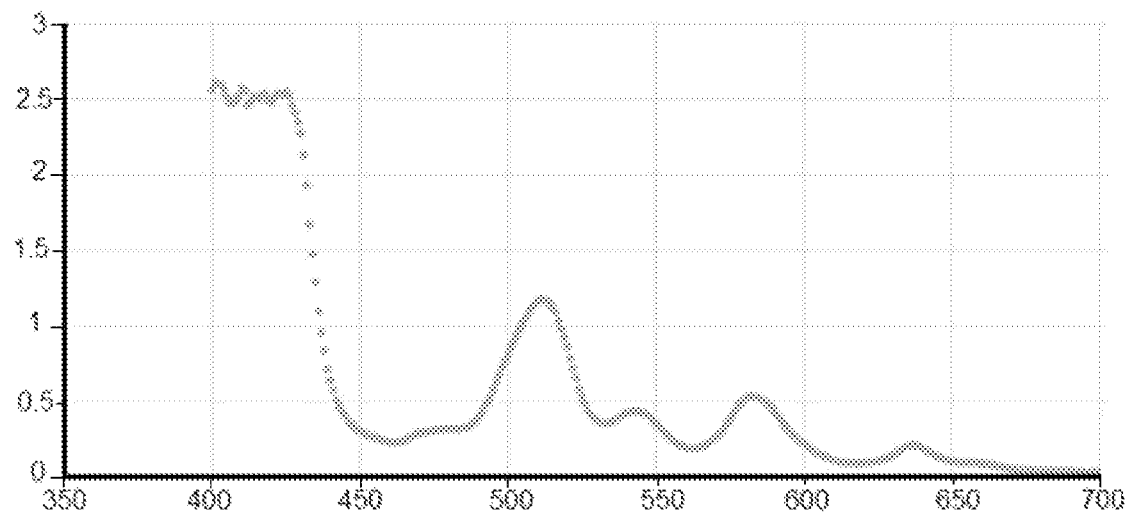
FIG. 4B shows the absorption spectra of Representative Compound 10.

1.4 Absorption spectrum: The absorption spectra of the Representative Compounds were acquired. The concentration of compound was 10 µM. FIG. 4A shows the absorption spectrum of Representative Compound 4 and FIG. 4B shows the absorption spectrum of Representative Compound 10.

Representative Compounds 4 and 10 have an absorption band at 660 nm and 637 nm, within the long wavelength range, respectively. Varying the concentration of the Representative Compounds in solution and mixed with protein did not change the absorption spectra obtained.

1.5 Biological testing of the Representative Compounds: To assess the activity of the Representative Compounds, in vitro testing was conducted.

1.5.1 Ras pulldown with inhibitor interference: Inhibition of compounds on binding between Ras and Ras-binding domain (RBD) of Rafl was firstly analysed using Active Ras PullDown and Detection Kit (Thermofisher Scientific, Catalogue no 16117). The protocol was in accordance with the manual supplied with the kit. Western blot analysis was used to measure the inhibition. The known Inhibitor Kobe0065 was purchased from Focus Biosciences, Australia (www.focusbio.com.au) and used as the positive control.

1.5.2 ELIZA Assay: Another method to detect the inhibition of the Representative Compounds used a Ras activation ELIZA kit (Merck Millipore, Cat no 17-497). The protocol was in accordance with the manual provided with the kit. The inhibition was measured using a Chemiluminescent imaging system. The known inhibitor Kobe0065 was purchased from Focus Biosciences, Australia (www.focusbio.com.au) and used as the positive control.

Figure 5A:
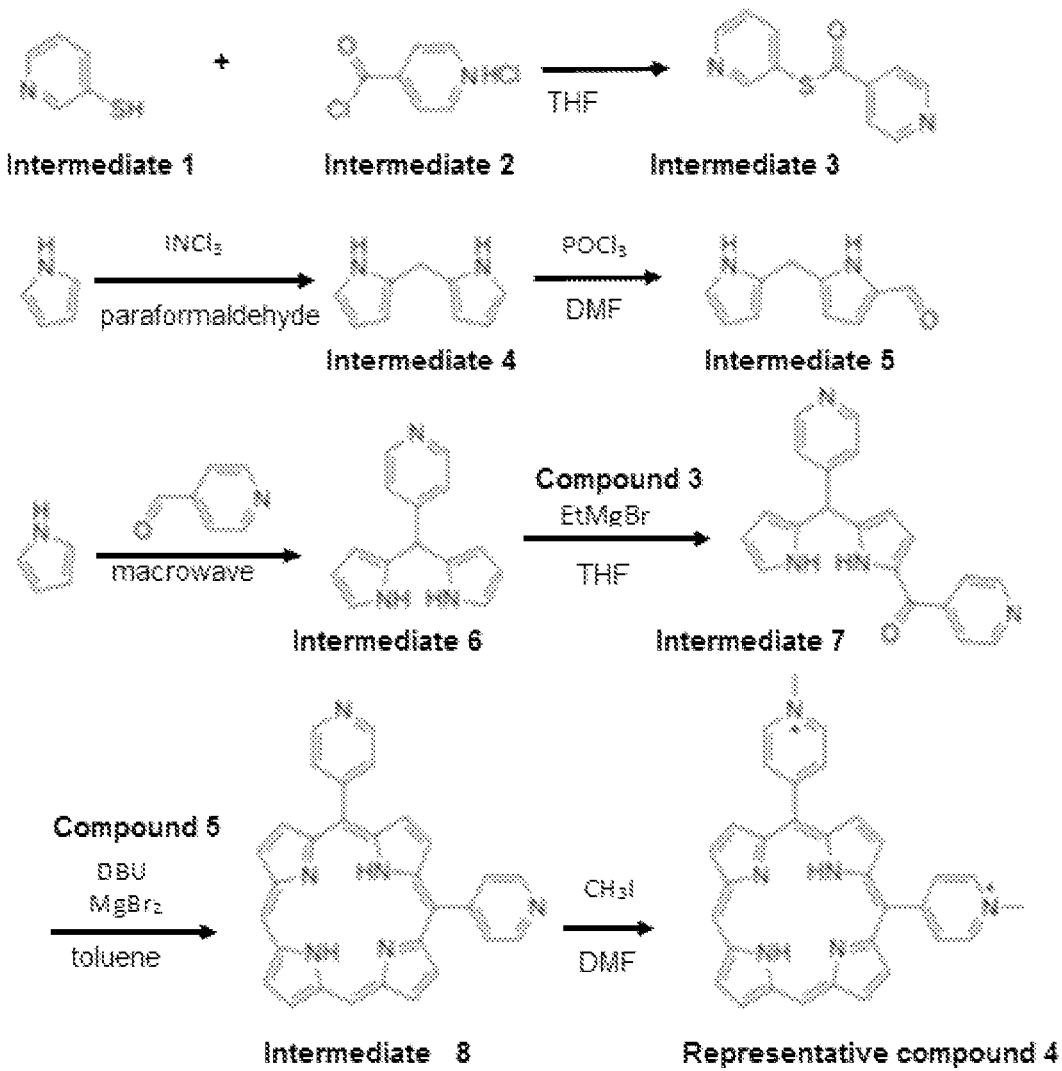
FIG. 5A shows the synthetic pathway followed for production of Representative Compound 4.

1.6 Synthesis of Representative Compound 4: The pathway for synthesis of Representative Compound 4 is shown in FIG. 5A.

Yields reported herein refer to purified products (unless specified) and are not optimised. Analytical TLC was performed on Merck silica gel 60 F254 aluminium-backed plates. Compounds were visualised by UV light and/or stained with either 12 or potassium permanganate solution followed by heating. Flash column chromatography was performed on silica gel. 1H-NMR spectra were recorded on a Bruker Avance-400 MHz spectrometer with a BBO (Broad Band Observe) and BBFO (Broad Band Fluorine Observe) probe. Chemical shifts (δ) are expressed in parts per million (ppm) downfield by reference to tetramethylsilane as the internal standard. Splitting patterns are designated as s (singlet), d (doublet), m (multiplet) and br s (broad singlet). Coupling constants (J) are given in hertz (Hz). LCMS analyses were performed on an Acquity BEH Hillic (2.10× 100 mm, 1.70 µm) using the Electrospray Ionisation (ESI) technique.

Synthesis of Intermediate 3: To a 25 mL three-necked flask, pyridine-3-thiol (2.0 g, 18.0 mmol, 1.0 eq), isonicotinoyl chloride hydrochloride (3.2 g, 18.0 mmol, 1.0 eq) and THF (40.0 mL) were added. The resulting mixture was stirred overnight at ambient temperature. The reaction was monitored by TLC & LCMS, which showed the starting material was consumed. The reaction mixture was filtered and the cake was washed with hexane. Then the cake was treated with biphasic solution of $Et_2O$ and sat. $NaHCO_3$ until no bubbles were observed. The resulting mixture was repeatedly extracted with $Et_2O$. The combined organic phase was dried over $Na_2SO_4$ and concentrated under reduced pressure. The crude product was dissolved in THF (2.0 mL), then 20 mL hexane was added to the solvent to form a precipitate. The crude product was recrystallized with THF and hexane. After filtration, 1.55 g light yellow solid was obtained. LC-MS and $^1H$ NMR spectra were obtained.

Synthesis of Intermediate 4: To a 100 mL three-necked flask equipped with a condenser and an internal thermometer, pyrrol (30.0 mL, 432 mmol) and paraformaldehyde (1.5 g, 50.0 mmol, 1.0 eq) were added. The resulting mixture was stirred for 0.1 h at 60° C. Subsequently, $InCl_3$ (1.1 g, 5.0 mmol, 0.1 eq) was added and the reaction was stirred for another 3 h at 60° C. Then the reaction was cooled to ambient temperature and NaOH powder (2.0 g) was added and stirred for 4 h. The reaction was monitored by TLC & LCMS, which showed that the starting material was consumed. The reaction mixture was filtered and the cake was repeatedly washed with pyrrol. The combined organic phase was concentrated under reduced pressure. The crude product was purified on a silica gel, eluting with EtOAc/Pet.ether at a ratio starting from 1/100 and gradually increasing to a ratio of 1/10. A 2.4 g white solid was obtained with a yield of 33%. A $^1$H NMR spectrum was obtained.

Synthesis of Intermediate 5: To a 50 mL three-necked flask, DMF (16.0 mL) was added. And the flask was cooled to 0° C. Then POCl$_3$ (0.6 mL, 3.02 mmol) was added dropwise to the reaction at 0° C. and stirred for 5 min to yield a Vilsmeier reagent. Subsequently, a cold (0° C.) solution of Compound 4 (1.0 g, 6.8 mmol, 1.0 eq) in DMF (3.0 mL) was added to the reaction dropwise. After the addition was completed, the final mixture was stirred at 0° C. for 2 h. Then a biphasic solution of ethyl acetate and saturated aqueous sodium acetate was added and stirred overnight. The reaction was monitored by TLC & LCMS, which showed the starting material was consumed. Ethyl acetate was separated from the reaction mixture and the aqueous solution was extracted with EtOAc (10 mL×3). The combined organic phase was washed with brine and dried over anhydrous Na$_2$SO$_4$. After concentration, under reduced pressure, the crude product was purified on a silica gel, eluting with EtOAc/Pet. ether at a ratio starting from 1/40 and gradually increasing to a ratio of 3/2. A 272 mg dark brown solid was obtained with a yield of 23%. LC-MS and $^1$H NMR spectra were obtained.

Synthesis of Intermediate 6: To a 20 mL glass tube, pyrrol (10.0 mL) and isonicotinaldehyde (10.0 mL) were added. The tube was sealed and heated to 150° C. and stirred for 20 min under microwave. The reaction was monitored by TLC & LCMS, which showed isonicotinaldehyde was consumed. The reaction mixture was cooled to ambient temperature and concentrated under reduce pressure. A crude brown solid product was purified on a silica gel, eluting with EtOAc/Pet.ether at a ratio starting from 1/50 and gradually increasing to a ratio of 1/2. A 2.4 g brown solid with a yield of 50% was produced. LC-MS and $^1$H NMR spectra were obtained.

Synthesis of Intermediate 7: To a 100 mL three-necked flask, Intermediate 6 (300.0 mg, 1.4 mmol, 1.0 eq) and THF (5.4 mL) were added. Then EtMgBr (3.5 mL, 1.0 mol/L) was added to the reaction at room temperature and stirred for 10 min. Subsequently, the reaction mixture was cooled to −70° C. with a cryopump. A solution of Intermediate 3 (324.0 mg, 1.4 mmol, 1.0 eq) in THF (5.4 mL) was added to the reaction dropwise and stirred for an additional 10 minutes before slowly warming up to ambient temperature. The reaction was stirred overnight. The reaction was monitored by TLC & LCMS, which showed that the starting material was consumed. The reaction was quenched by addition of saturated aqueous NH$_4$Cl and stirred for 15 min. The mixture was extracted with EtOAc (20 mL×3). The combined organic phase was washed with brine (30 mL×2) and dried over Na$_2$SO$_4$. After concentration, under reduced pressure, the crude product was purified on a silica gel, eluting with EtOAc/Pet.ether at a ratio starting from 1/20 and gradually increasing to a ratio of 1/2. A 320 mg black solid was produced with a yield of 70%. LC-MS and $^1$H-NMR spectra were obtained.

Synthesis of Intermediate 8: To a 250 mL three-necked flask, Compound 5 (250.0 mg, 1.4 mmol, 1.0 eq), Intermediate 7 (471.3 mg, 1.4 mmol, 1.0 eq), toluene (33.3 mL) and DBU (4.7 mL) were added. The mixture was stirred for 5 min at ambient temperature and then MgBr$_2$ (1.85 g, 10.0 mL, 7.0 eq) was added, which was then capped in atmosphere and heated to 115° C. with stirring overnight. The reaction was monitored by TLC & LCMS, which showed that the starting material was consumed. The reaction mixture was transferred to a 250 mL single-necked flask with THF and concentrated under reduce pressure. The crude product was dissolved in DCM and washed with deionised water followed by brine. Then the organic phase was acidified with TFA and neutralized with TEA. Then washed with deionised water and brine. The organic phase was dried over Na$_2$SO$_4$ and concentrated under reduced pressure and purified on a pre-TLC plate. About 10 mg of pure product and 40 mg with non-ideal purity was obtained. A LC-MS spectrum was obtained.

Figure 7A:
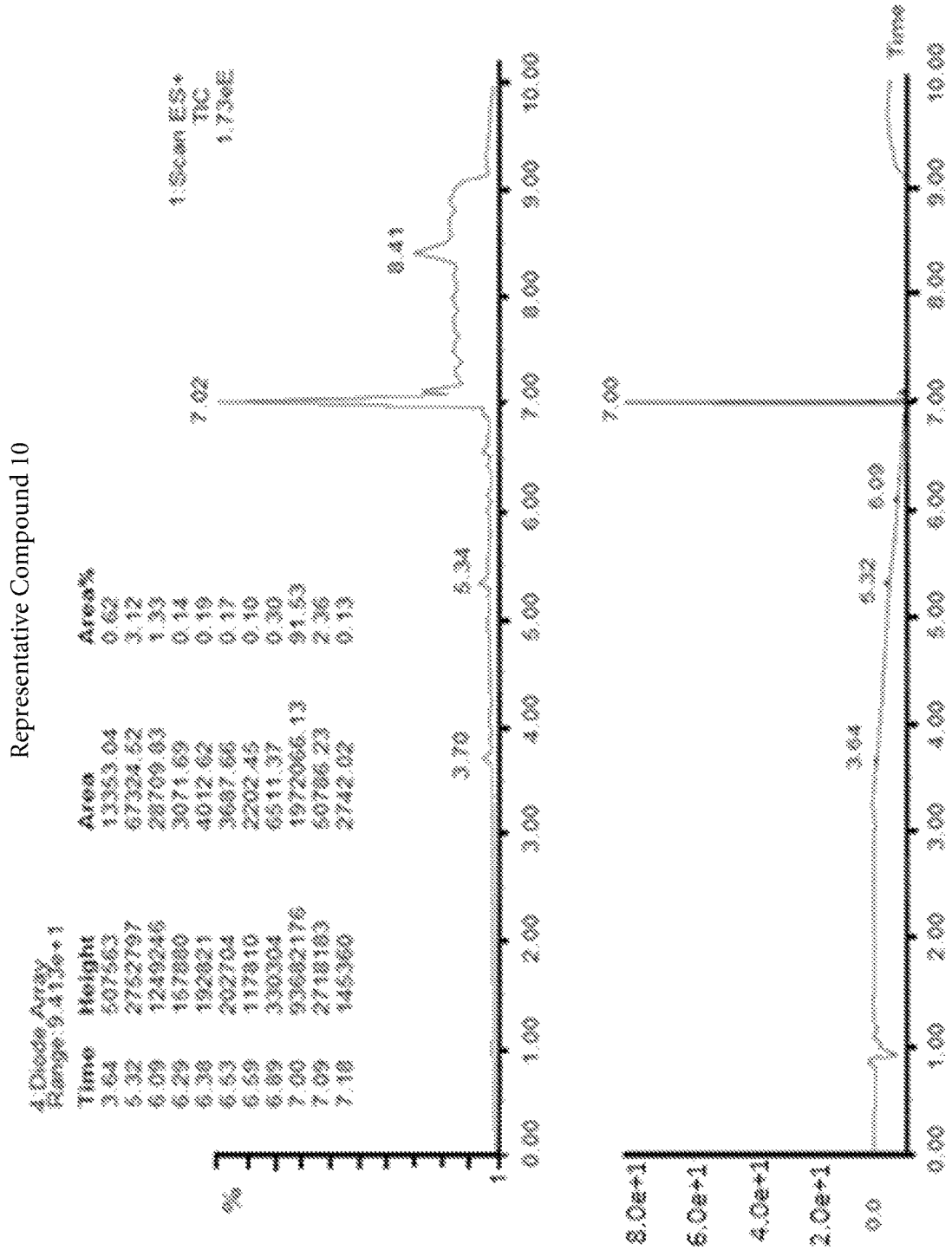
FIGS. 7A to 7C show the UPLC, UV-Vis and MS spectra, respectively, obtained for Representative Compound 10.
Figure 7B:
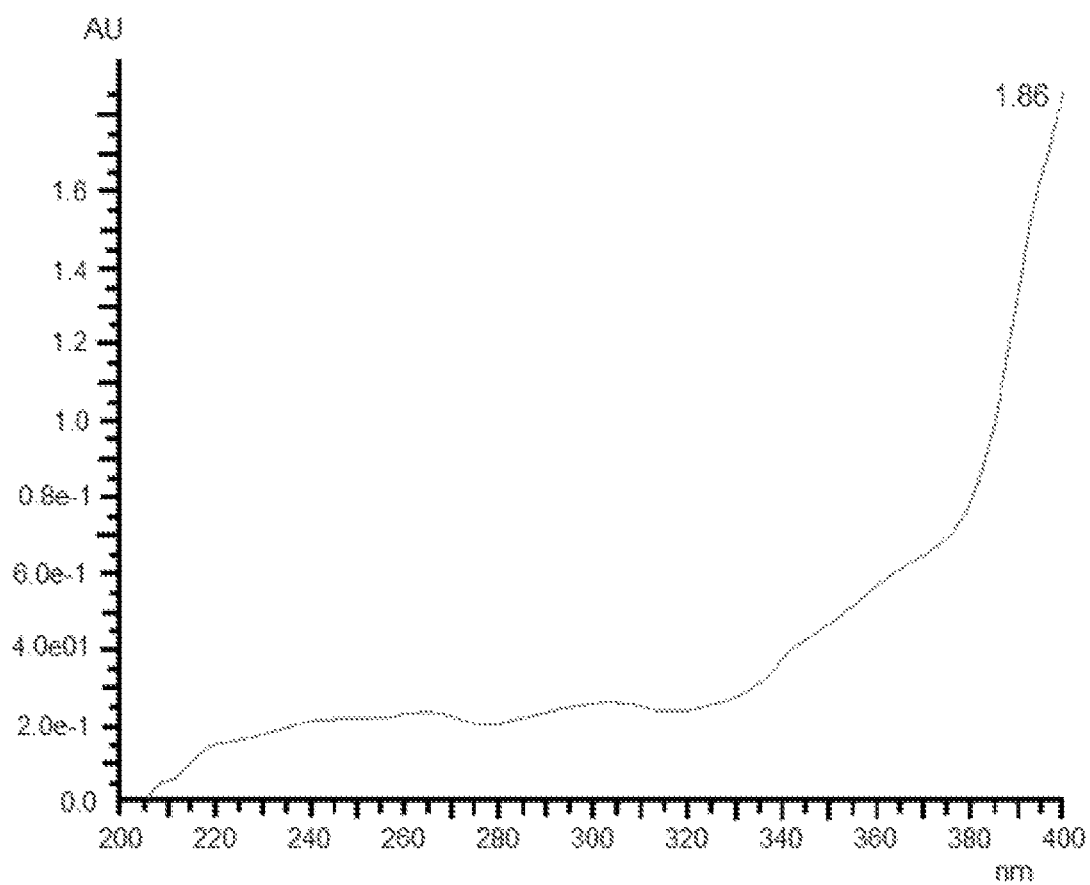
Figure 7C:
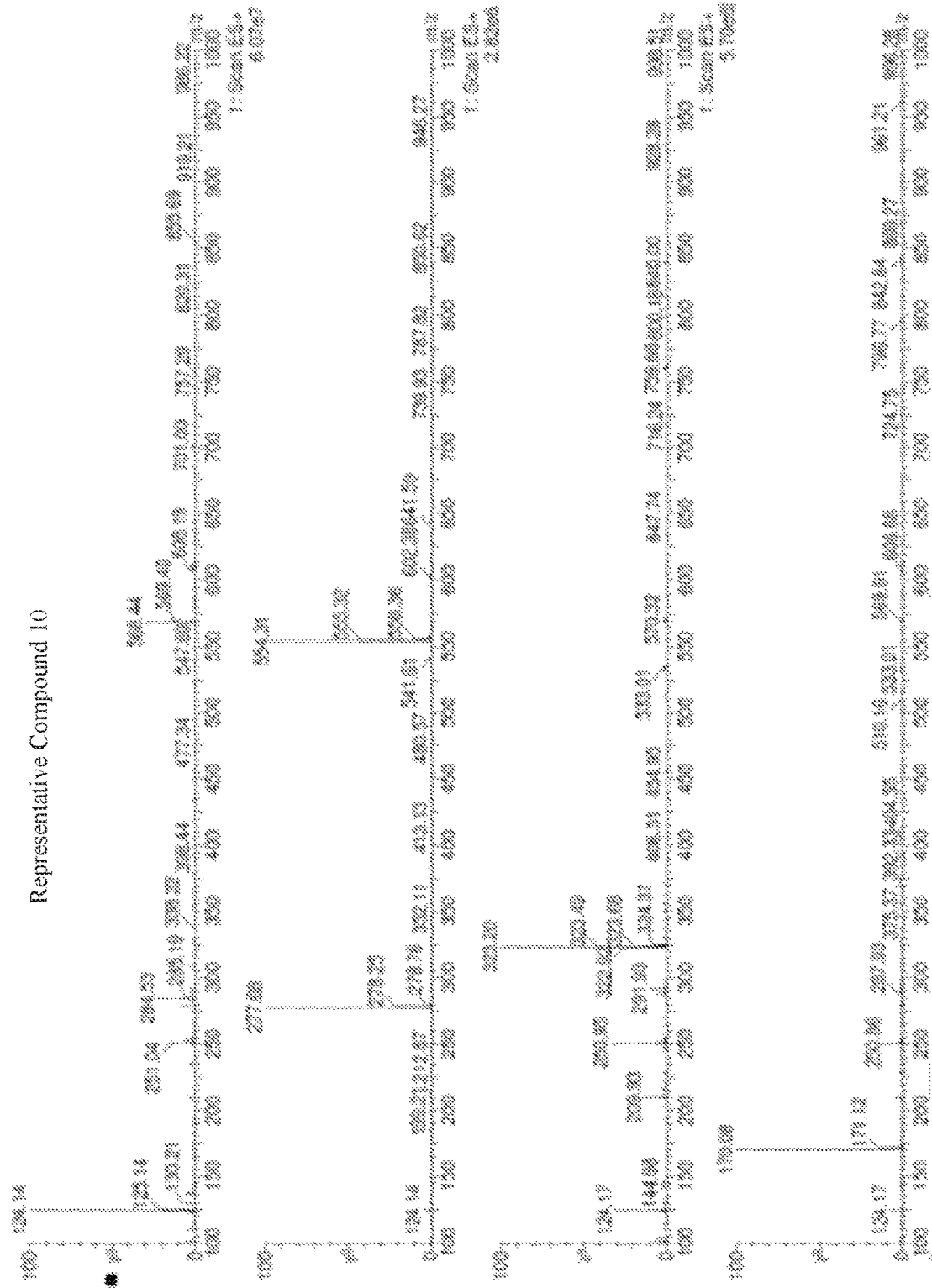
Figure 7D:
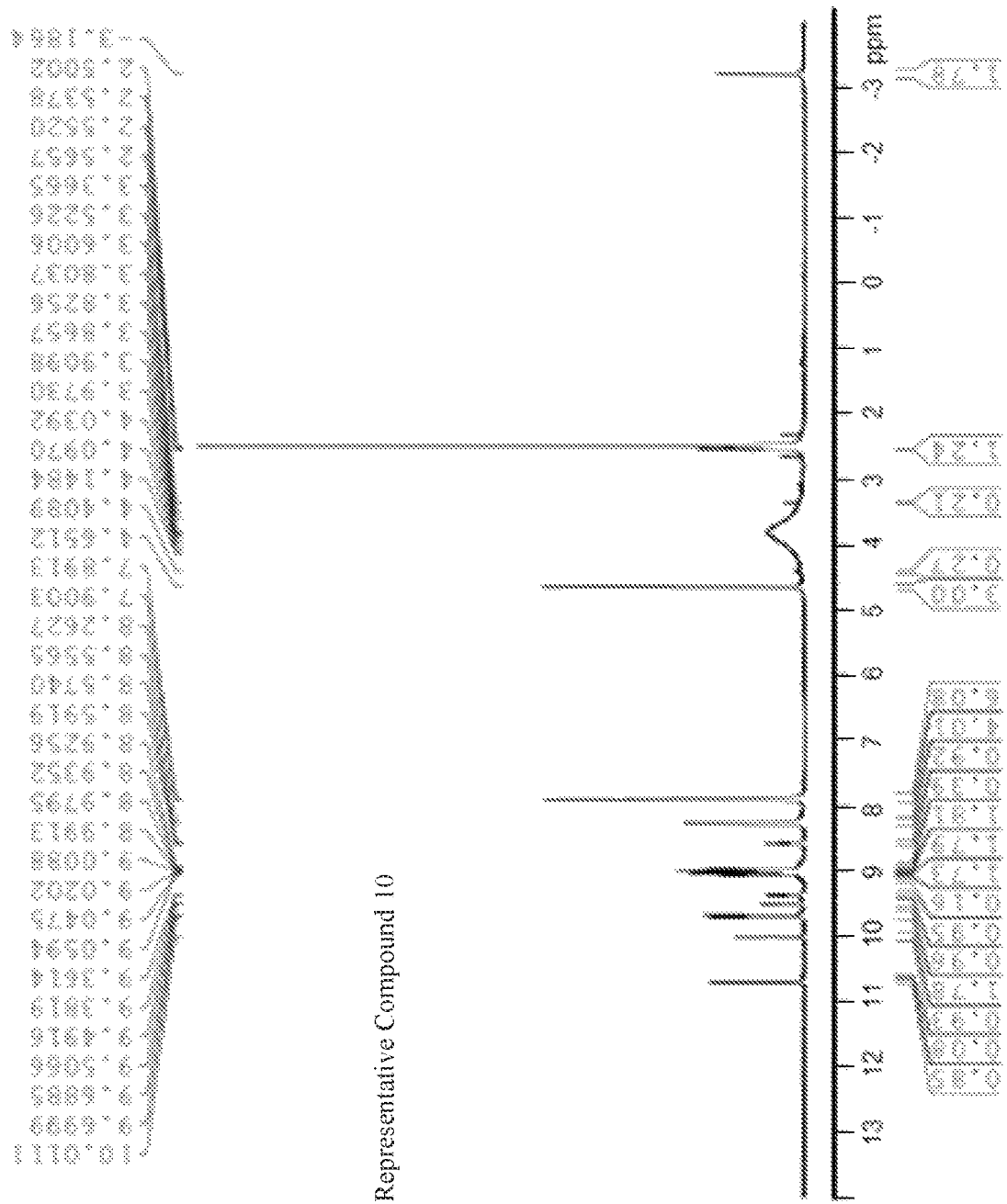
FIGS. 7D to 7I show the NMR spectra obtained for Representative Compound 10.
Figure 7E:
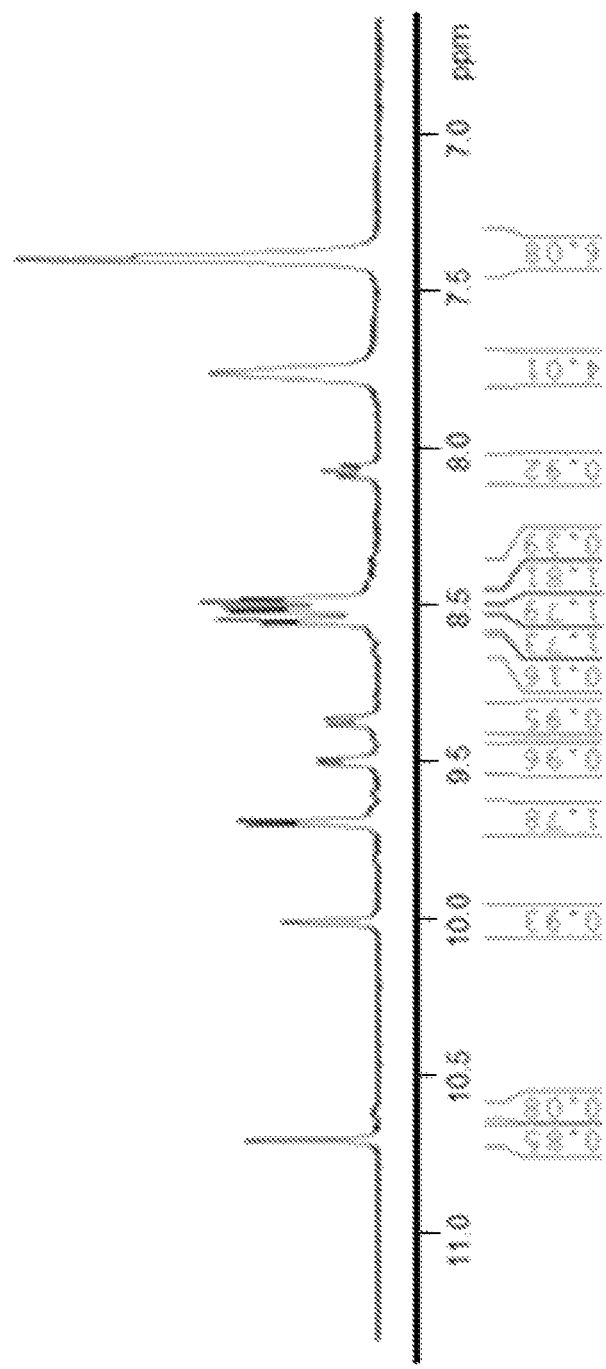
Figure 7F:
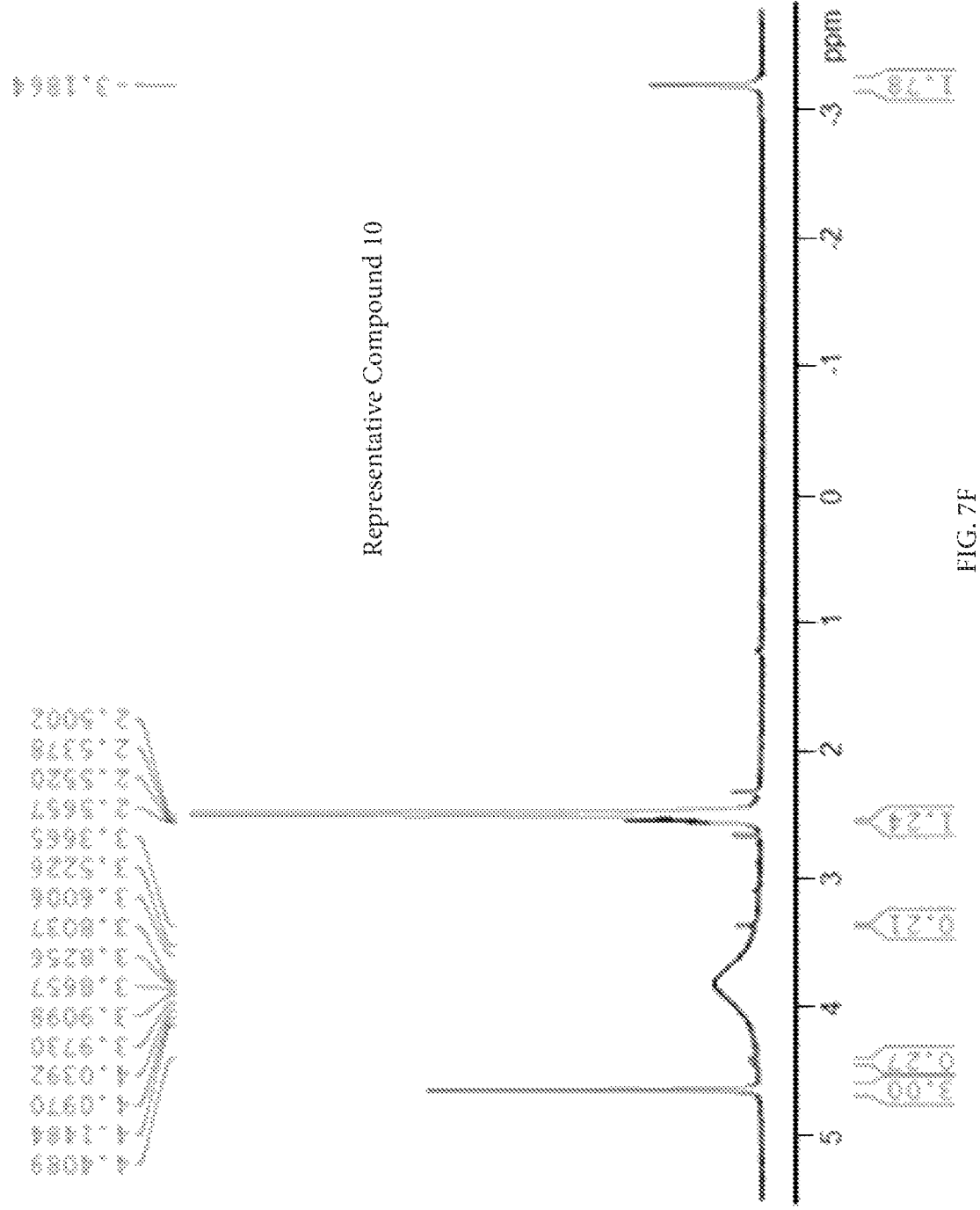
Figure 7G:
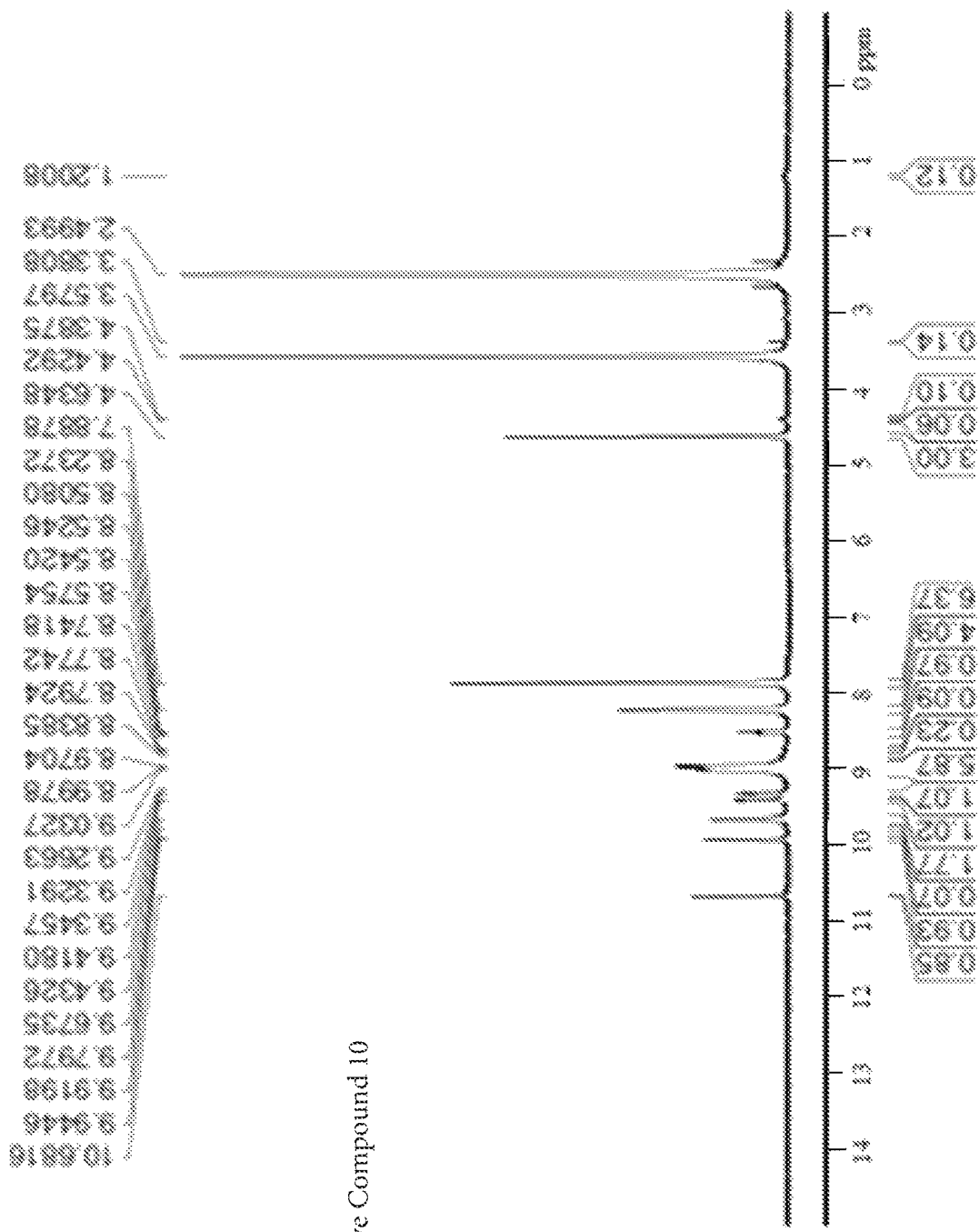
Figure 7H:
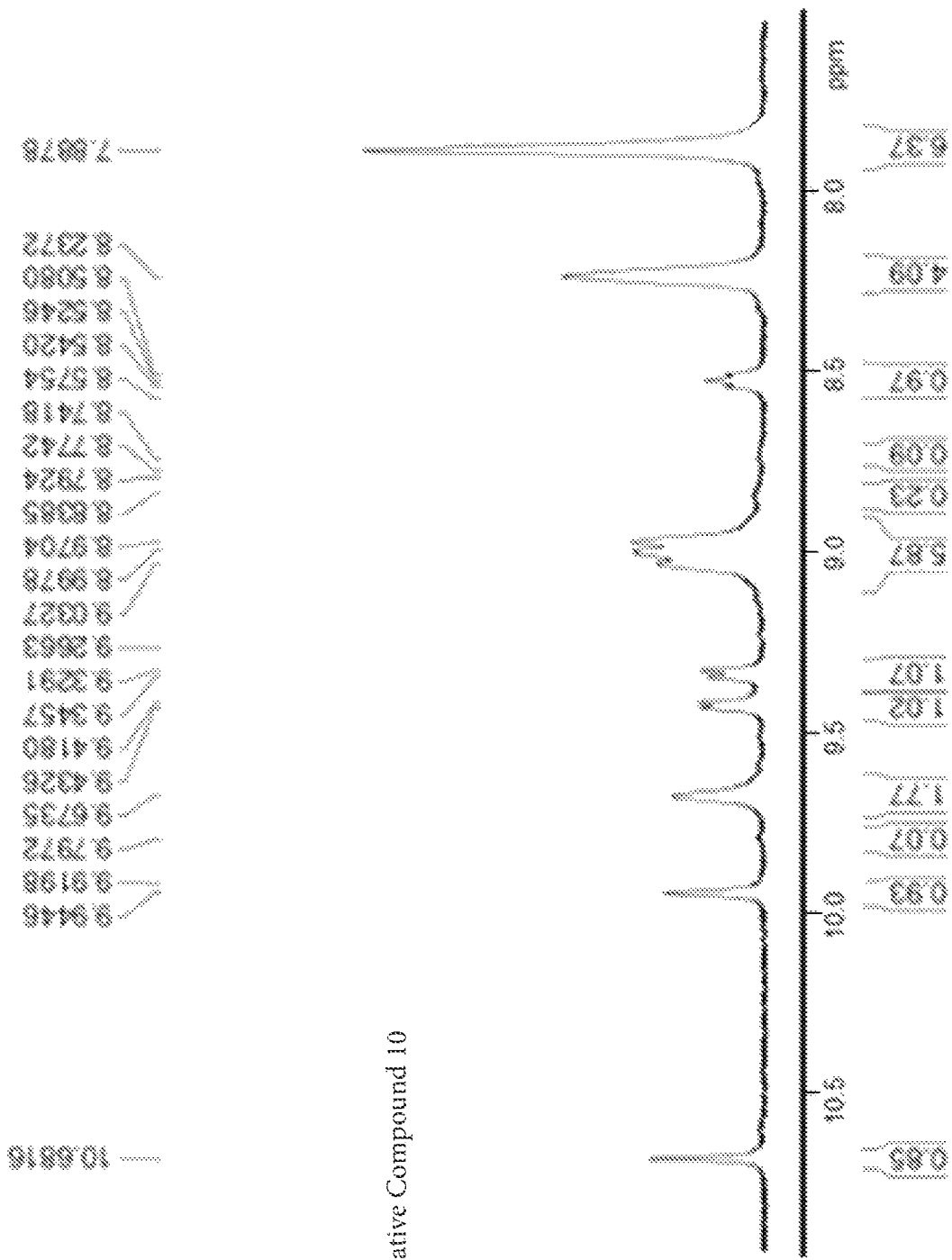
Figure 7I:
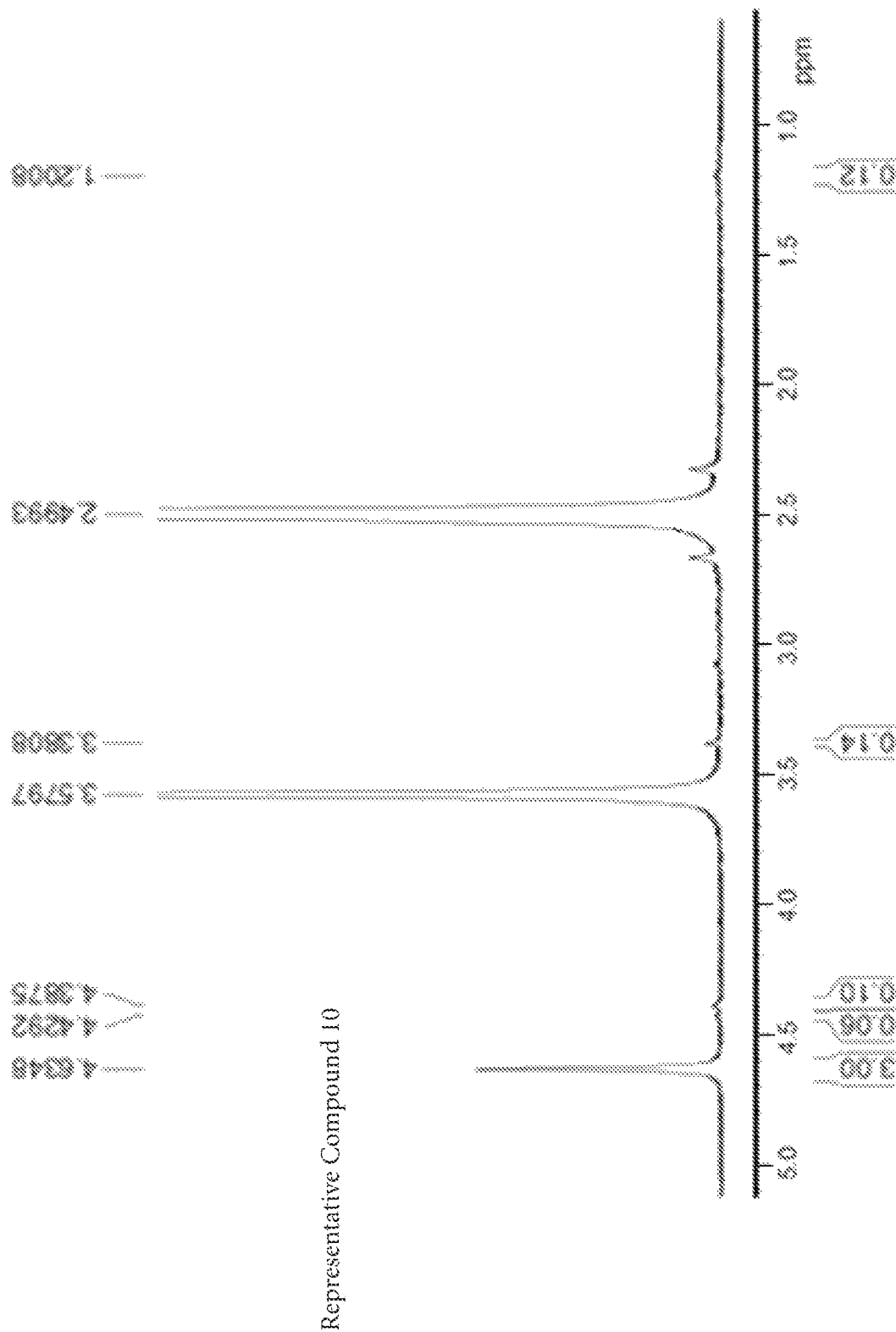

To a 50 mL round-bottomed flask, CH3I (1.0 mL) was added to a mixture of Intermediate 8 (40.0 mg, crude, 1.0 eq) in DMF (5.0 mL) at ambient temperature, the reaction mixture was stirred overnight at ambient temperature. The reaction was monitored by LCMS, which showed that the starting material was consumed. The reaction mixture was concentrated under reduced pressure and purified on a prep-HPLC with ACN/water at a ratio starting from 45/55 and gradually increasing to a ratio of 85/15. A 21 mg dark brown solid was obtained. LC-MS and $^1$H NMR spectra were obtained and are shown in FIGS. 7A and 7B, respectively.

Figure 5B:
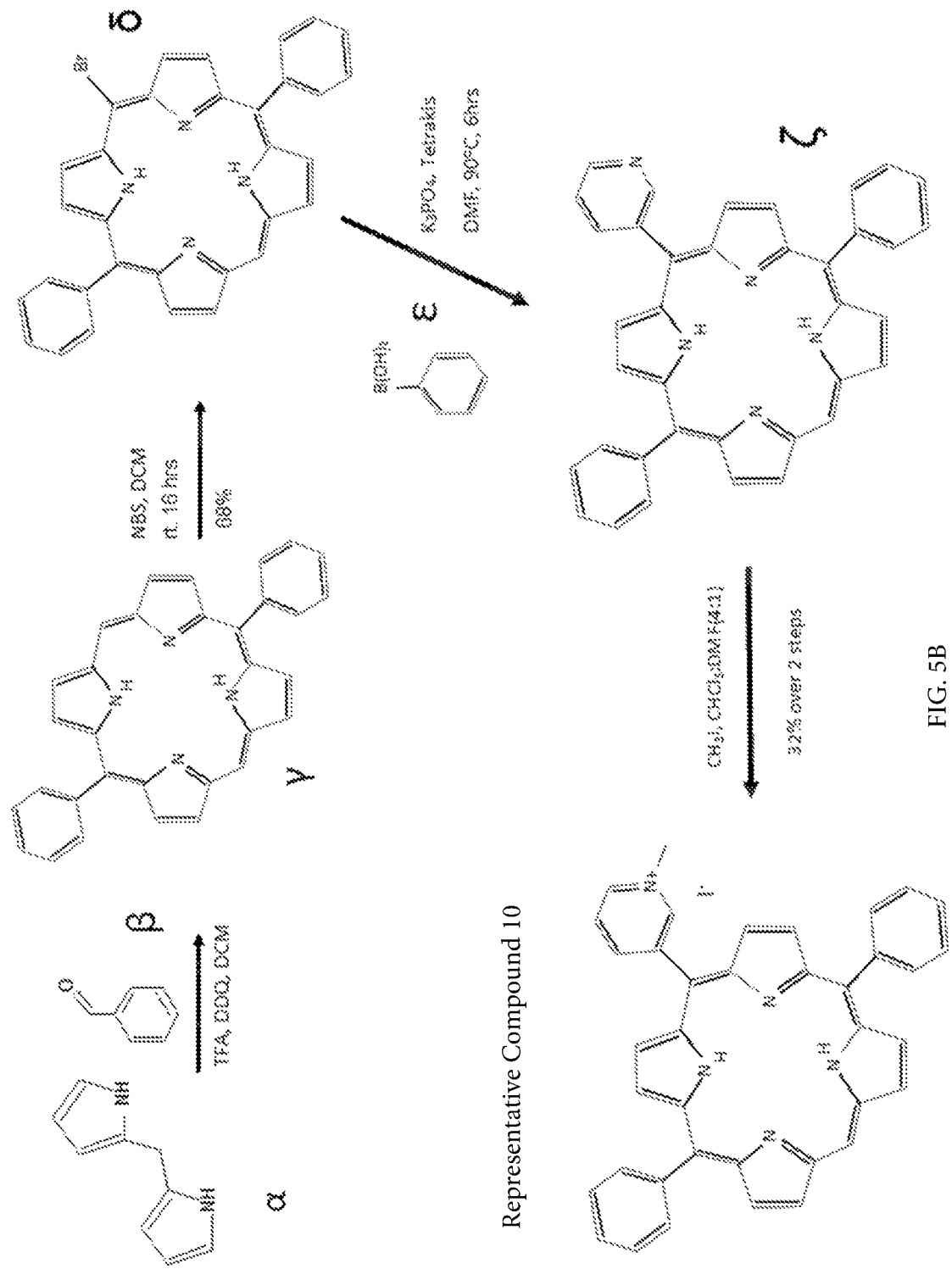
FIG. 5B shows the synthetic pathway followed for production of Representative Compound 10.
Figure 6A:
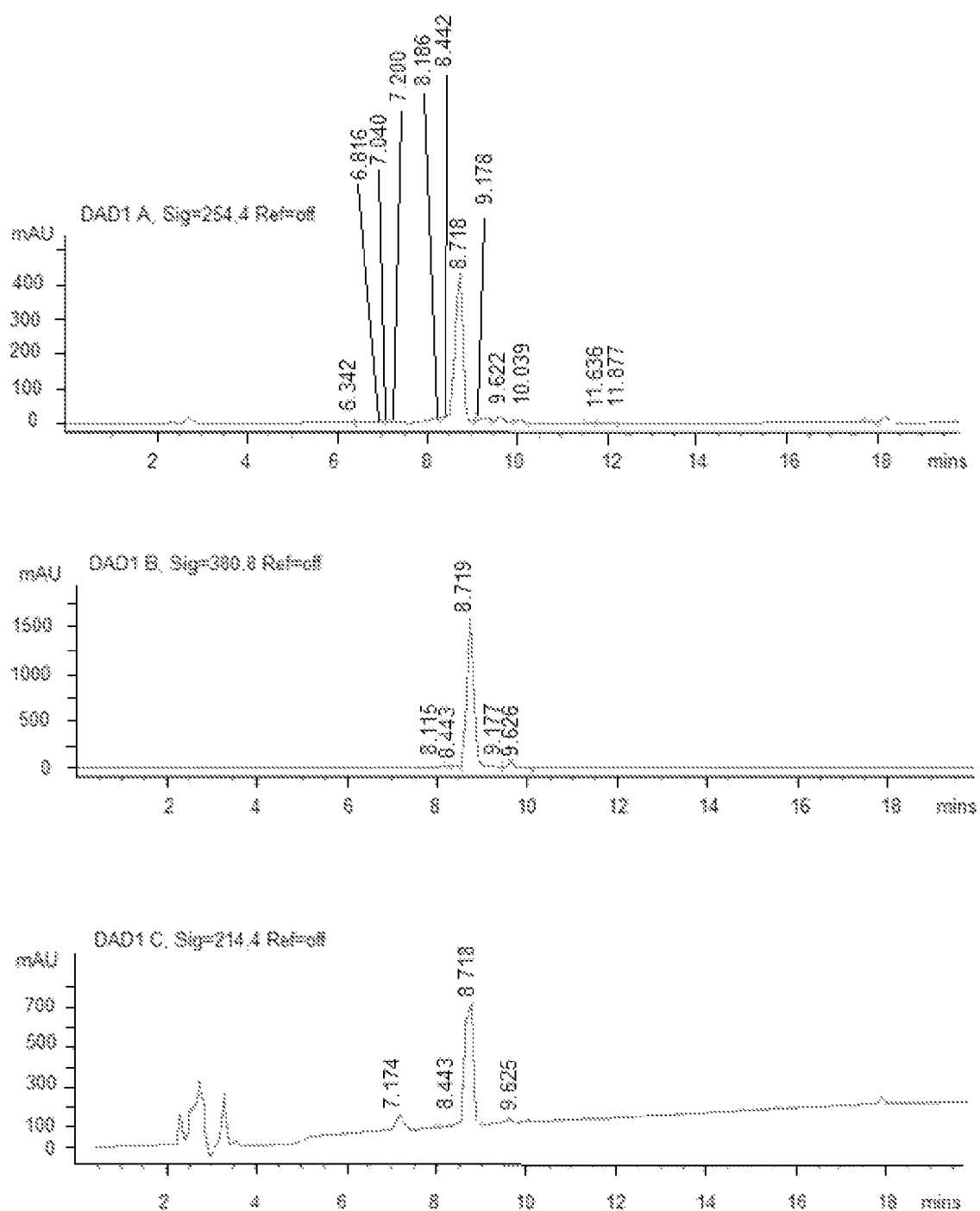
FIG. 6A shows the HPLC spectra obtained for Representative Compound 4.
Figure 6B:
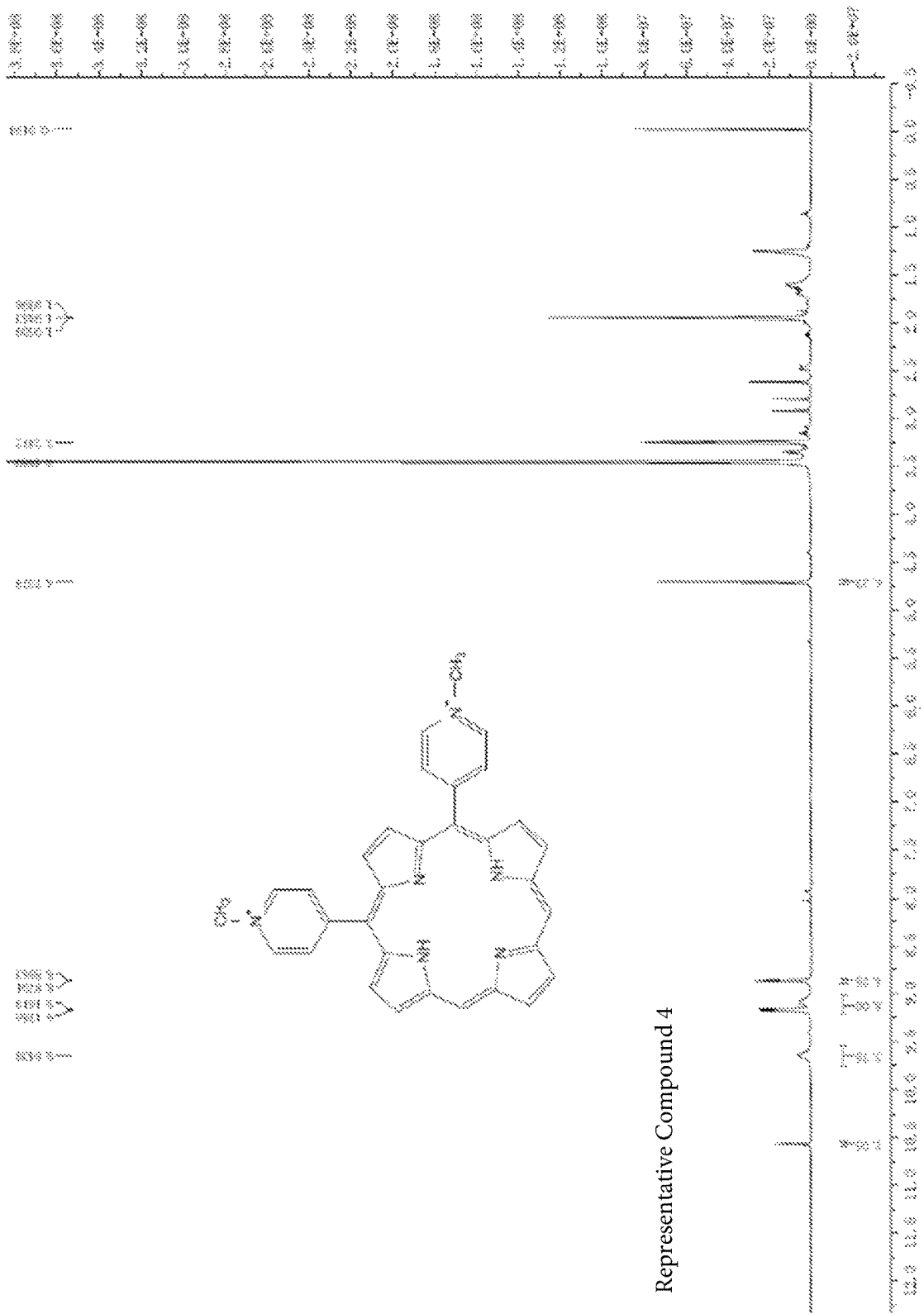
FIG. 6B shows the NMR spectra obtained for Representative Compound 4.

1.7 Synthesis of Representative Compound 10: The pathway for synthesis of Representative Compound 10 is shown in FIG. 5B.

Preparation of 5,15-diphenylporphyrin (γ): To an ice-cold solution of dipyrrolmethane (α) (2.0 g, 13.70 mmol) in DCM was added benzaldehyde (β) (1.41 mL, 13.96 mmol) followed by the dropwise addition of TFA (0.23 mL, 3.15 mmol) at 0° C. The resulting reaction mixture was stirred for 3 h at 0° C. followed by the addition of DDQ (3.72 g, 16.44 mmol). The resulting mixture was stirred at room temperature for 4 hrs. After completion of reaction (TLC monitoring), the reaction was quenched with Et$_3$N (10.0 mL) and stirred for 5 min at room temperature. The organic was concentrated under reduced pressure and the crude material was purified over silica gel (100-200 M) column chromatography, elution with 30% DCM in hexanes to obtain the desired product γ (0.78 g, yield: 12%) as a purple coloured solid. A $^1$H-NMR spectrum was obtained.

Preparation of 10-bromo-5,15-diphenylporphyrin (δ): To an ice-cold solution of 5,15-diphenylporphyrin (γ) (500 mg, 1.08 mmol) in DCM (500 mL) was added NBS (153 mg, 0.85 mmol). The mixture was then stirred at room temperature for 16 h. After completion of reaction (TLC monitoring), the reaction mixture was washed with water (3×500 mL) and organic layer was dried over Na$_2$SO$_4$, filtered and concentrated under reduced pressure. The crude thus obtained was purified over silica gel (100-200 M) column chromatography, elution with 10% DCM in hexanes to get desired product (δ) (400 mg, yield: 68%) as a purple coloured solid. A $^1$H-NMR spectrum was obtained.

Preparation of 5,15-diphenyl-10-(pyridin-3-yl)porphyrin (ζ): To a stirred solution of 10-bromo-5,15-diphenylporphyrin (δ) (75 mg, 0.14 mmol) in DMF (10 mL) was added pyridin-3-yl boronic acid (ε) (49 mg, 0.40 mmol) and potassium phosphate (96 mg, 0.41 mmol) at room temperature. The resulting reaction mixture was degassed with N$_2$ for 15 min followed by the addition of tetrakis(triphenylphosphine)palladium (θ) (16 mg, 0.014 mmol) and heated at 90° C. for 6 h. After completion of reaction (TLC monitoring), the reaction mixture was quenched with ice-cold water (100 mL) followed by the extraction of the crude compound with EtOAc (3×100 mL). The combined organic phase was washed with water, brine solution, then dried over Na$_2$SO$_4$ and filtered. The organic phase was evaporated under reduced pressure to obtain the crude compound (ζ) (90 mg) as a purple coloured solid which was carried forward to the next step without further purification. A $^1$H-NMR spectrum was obtained.

Preparation of 3-(10,20-diphenylporphyrin-5-yl)-1-methylpyridin-1-ium iodide (Representative Compound 10): To a stirred solution of 5,15-diphenyl-10-(pyridin-3-yl)porphyrin (ζ) (90 mg, 0.17 mmol) in a mixture of DMF:CHCl$_3$ (20:80 mL) was added methyl iodide (8.0 mL) at room temperature. The resulting mixture was stirred for 8 h at room temperature. After completion of reaction (TLC monitoring), the solvent was evaporated under reduced temperature until about 10.0 mL was left in the crude reaction mixture. Diethyl ether (100 mL) was added to obtain a precipitate and the solvent was decanted from the vessel. The crude material was further re-crystallized with ethanol and diethyl ether to obtain the desired Representative Compound 10 (30.0 mg, 32% over 2 steps). A $^1$H-NMR spectra was obtained. UPLC and $^1$H-NMR spectra were obtained and are shown in FIGS.

1.8 Cells: Human cell lines were obtained from the NIH cell culture and cultured in media recommended by supplier.

1.9: Cell Proliferation Assays: Cells (2-3000) were seeded in a 96-well plate and cultured in McCoy's 5 containing 10% (vol/vol) FBS in the presence of one of compounds. Viable cell numbers were measured using a fluorometric kit ("Cell Titre-Blue Cell Viability Assay": Promega Inc, USA). The viable cells convert blue colour dye to red/pink after incubating at 37 degrees with 5% CO$_2$.

2. Results 2.1. Inhibition of Ras-Raf binding: Inhibition of Ras-Raf binding was measured for several compounds as shown in Table 2. Kobe0065 was used as a positive control. Table 2 shows an inhibition of IC$_{50}$ (10 to 50 µM) from Ras pulldown assay and IC$_{50}$ (<10 µM) from Ras activation ELIZA assay, consistent with the previous results (Shima F et al., PNAS, 2013, 110, 8182). With the inhibition by Kobe0065 confirmed, the assay kit has therefore been verified.

Representative Compound 1 is commercially available from the market and was purchased from PorphyChem SAS, France (www.porphychem.com). The analysis showed an inhibition IC$_{50}$ of 10-50 µM with the Ras pulldown assay, similar to the activity of Kobe0065. However, the inhibition was much weaker in the Ras activation ELIZA assay. While not wanting to be bound by any one theory, the inventors hypothesise that compounds of the invention are neutral porphyrin compounds, the activation of which might be sensitive to the conditions used in different assay kits.

Representative Compound 12 is also commercially available from the market and was purchased from PorphyChem SAS, France (www.porphychem.com). The analysis showed an inhibition IC$_{50}$ of <10 µM with the Ras pulldown assay. Representative Compound 12 has 55% inhibition at 50 µM with the ELIZA assay. However, at the lower concentration (10 µM) the ELIZA assay resulted in a significant dark background. In the Ras pulldown assay, the inhibition also decreased as the concentration increased. The inhibition decreased from 68% at 50 µM to 20% at 100 µM. Without wanting to be bound by any one theory, the inventors hypothesise that because this compound is highly charged with a net charge of +4, significant electrostatic interactions with the ELIZA assay may result. Again, without wanting to be bound by any one theory, Representative Compound 12 could also bind to the regions of Ras nearby the Switch I, and act as an enhancer for Ras-Raf binding when the concentration increases.

Both Representative Compounds 4 and 5 were synthesized, but only Representative Compound 4 can be synthesised and tested by ELIZA assay. The inhibition was 70.54% at 10 µM and 62.74% at 50 µM. The decrease correlating to the concentration is similar to that experienced with Representative Compound 12. Again, while not wanting to be bound by any one theory, the inventors hypothesise that because this compound is positively charged with net charge of +2, electrostatic interactions may also be at play. However, the size of Representative Compound 4 is relatively smaller and less hydrophobic.

Representative Compound 10 was designed and synthesised. Only an ELIZA assay test was carried out. The inhibition was 35.2% at 10 µM. Representative Compound 10 is also positively charged with a net charge of +1.

2.2. Cell Mortality: Oncogenic Ras has been involved in 30% of human cancer types, as listed in the prior art Table 3 from Alberto Fernandez-Medarde and Eugenio Santos Genes & Cancer, 2011, 2(3) 344-358. Two cell-lines were tested in further animal studies and for clinical indication purposes. The colon-cancer cell line (HCT-116) was tested.

Figure 8:
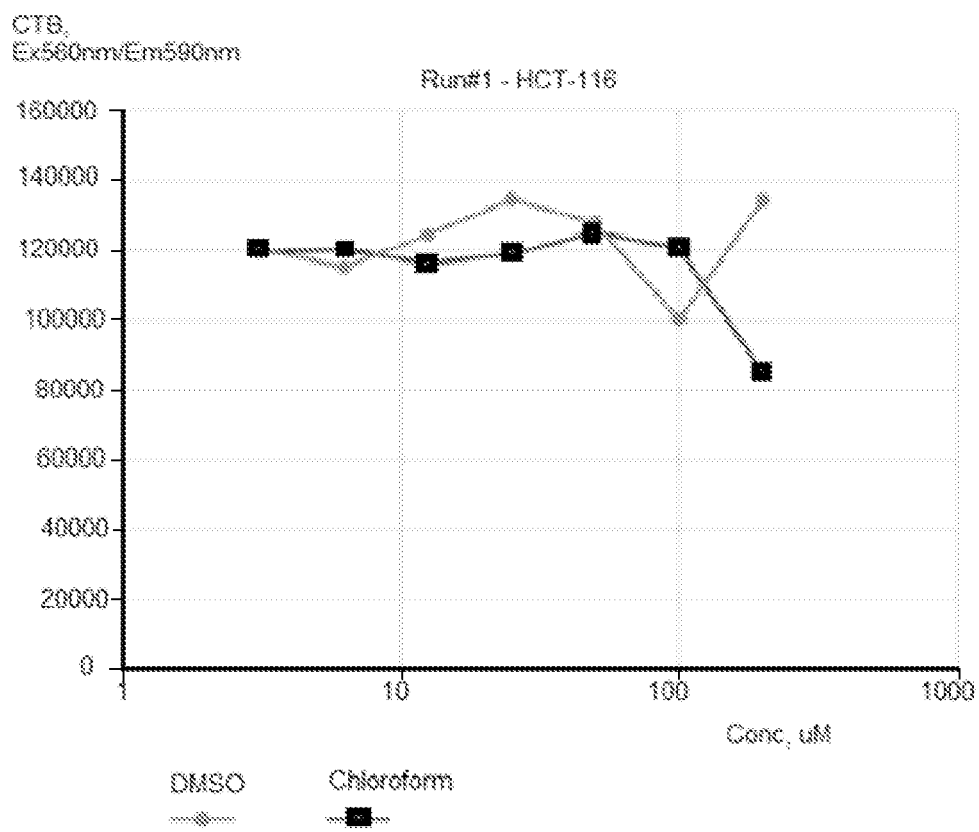
FIG. 8 is a line graph showing the inhibitory effects in solvent on the growth of HCT-116 cells.

The results of a cell-based assay with DMSO and chloroform are shown in FIG. 8. The solvent effects on the cell-growth are shown to be minimal.

Figure 9:
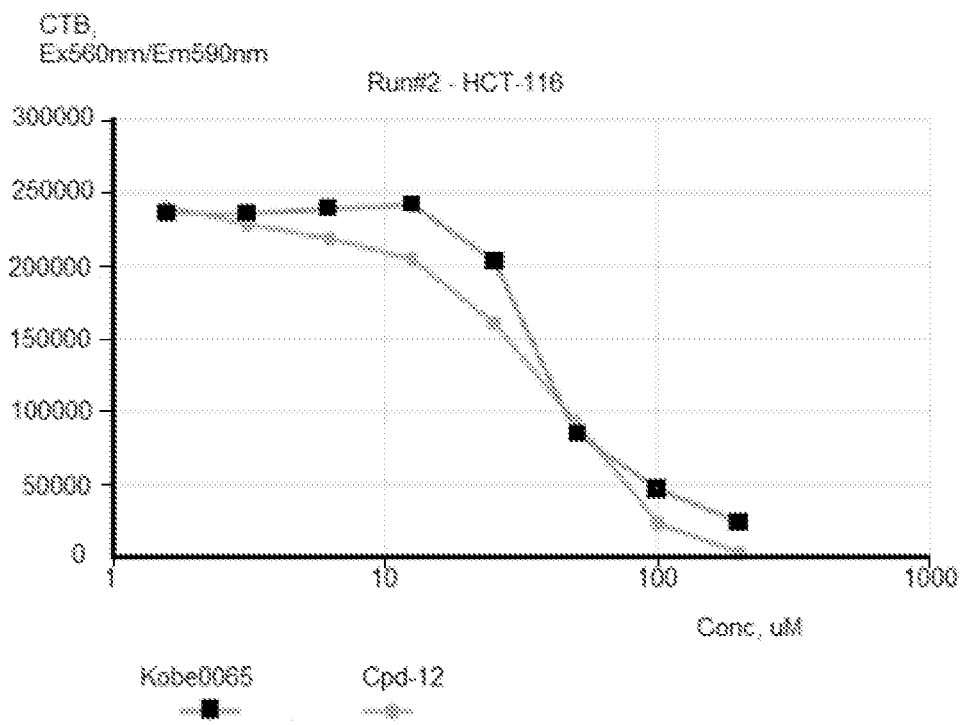
FIG. 9 is a line graph showing the inhibitory effects in solvent of Kobe0065 (control) and Compound 12 on the growth of HCT-116 cells.

Kobe0065 has been shown to be inhibitory on the H-rasG12V-transformed NIH 3T3 cells with an IC$_{50}$ of 0.5 to 2 µM (Shima et al., Proc. Natl. Acad. Sci. U.S.A. 2013, 110(20):8182). This compound was confirmed as an inhibitor of HCT-116 with an IC$_{50}$ of 20 to as shown in FIG. 9. The difference in IC$_{50}$ could be due to the different protocol and cell-line used. In addition, Representative Compound 12 is also an inhibitor of HCT-116 with an IC$_{50}$ comparable to Kobe0065. This compound has been also shown to reduce the cell-growth of human ovarian carcinoma cell-line (A2780), but only with light induction (Liu et al., Oncology Letters, 2014, 8:409).

Figure 10:
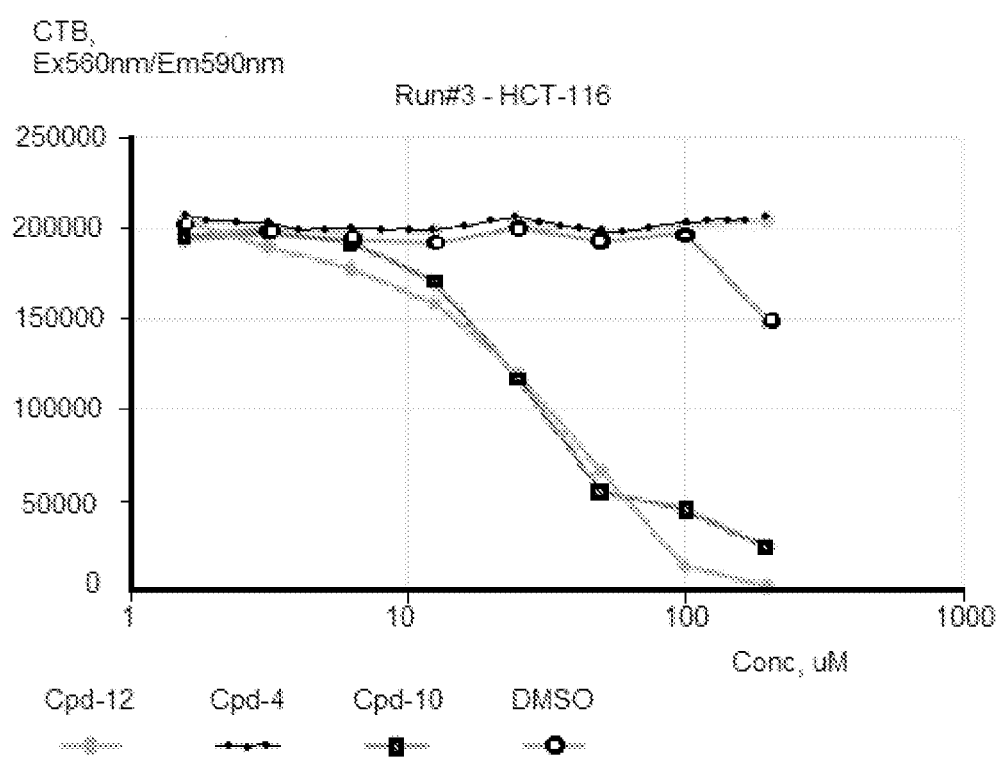
FIG. 10 is a line graph showing inhibition of Compounds 4, 10 and 12 on the growth of HCT-116.

FIG. 10 shows Representative Compound 10 to inhibit cell growth of HCT-116 with an IC$_{50}$ of 20 to 25 comparable to the Kobe0065 and Compound 12.

3. Conclusions

The inventors have developed a series of new generation photosensitisers for Photodynamic Therapy. This new generation of photosensitisers comprises an absorption band at greater than 620 nm and are positively charged.

The new generation of photosensitisers target the Switch I region of oncogenic Ras. The compounds have functional groups which specifically interact with the negatively charged residues Asp33, Glu37 and Asp38 of Switch I and can fit into the shallow cavity formed by these charged residues and a polar residues Leu19, Val29 and Thr35.

This new generation of photosensitisers have been demonstrated to disrupt the Ras-Raf binding in tumour cells. The effective concentration of these photosensitisers is at a low micromolar level, because at higher concentration, the compounds act as Ras-Raf binding enhancers.

While not wanting to be bound by any one theory, the inventors propose a cancer treatment strategy comprising two-steps: i) using the new generation of photosensitisers as chemotherapeutic agents to slow and/or reduce tumour growth; and ii) using photodynamic therapy to activate the photosensitiser to effectively kill the cancer cells.

The inventors have also provided new synthetic routes for the generation of new photosensitiser compounds.

Herein a new generation of photodynamic therapeutic agents for treatment of complex cancers is disclosed. These compounds have been designed and synthesised to block Ras-Raf interactions.

The in vitro assay (Ras pulldown and Eliza) demonstrated the inhibitory activity of selected compounds tested. The cell based assays investigated and demonstrated the cell mortality of selected compounds.

In this specification, the terms "comprises", "comprising" or similar terms are intended to mean a non-exclusive inclusion, such that an apparatus that comprises a list of elements does not include those elements solely, but may well include other elements not listed.

Throughout the specification the aim has been to describe the invention without limiting the invention to any one embodiment or specific collection of features. Persons skilled in the relevant art may realize variations from the specific embodiments that will nonetheless fall within the scope of the invention.

REFERENCES

Huang Z et al., Technol. Cancer Res. Treatment, 2008, 7:309-320.
Castano A P et al., Photodiagnosis Photodyn. Ther. 2004 1:279-93.
Castano A P et al., Photodiagnosis Photodyn. Ther. 2004 1:279-93;
Caetano A P et al Photodiagn. Photodyn. Ther. 2005, 2:91
Fernandez-Medarde A. Santos E., Gene and Cancer, 2(3) 344, 2011
McCormick F. & Wittinghofer A., Curr. Opin. Biotech. 1996, 7:449
Barbacid M, Annu. Rev. Biochem. 1987, 56:779
Baker N M and Der C J, Nature 2013, 497:577-578
Shima F et al, PNAS, 2013, 110:8182
Caflisch A, Karplus M., J Comput.-Aided Mol. Des. 1996, 10:372.
Zeng J. Comb. Chem. High Throughput Screen. 3:355
Thermofisher Scientific, Catalogue no 16117
Merck Millipore, Cat no 17-497
Liu et al., Oncology Letters, 2014, 8:409
Avci P, Guta A, et al., Low-Level Laser (Light) Therapy (LLLT) in Skin: Stimulating, Healing, Restoring (2013) Seminars in Cutaneous Medicine and Surgery, 32(1):41-52

TABLES

TABLE 1

List of Designated Compounds with Porphyrin Core

| Compound | R1 | R2 | R3 | R4 |
|---|---|---|---|---|
| Porphyrine | H | H | H | H |
| 1 | 4-pyridine | 4-pyridine | 4-pyridine | 4-pyridine |
| 2 | 4-pyridine | 4-pyridine | H | H |
| 3 | 4-pyridine | 4-pyridine | phenyl | phenyl |
| 4 | 4-methylpyridinium | 4-methylpyridinium | H | H |
| 5 | methylpyridinium-4-yl | 4-methylpyridinium | phenyl | phenyl |
| 6 | 4-methylpyridinium | 4-methylpyridinium | CH=CH2—CH3 | CH=CH2—CH3 |
| 7 | 4-methylpyridinium | 4-methylpyridinium | OH | OH |
| 8 | 4-methylpyridinium | Phenyl | phenyl | H |
| 9 | 4-methylpyridinium | Phenyl | phenyl | CH3 |
| 10 | methylpyridinium-3-yl | Phenyl | phenyl | H |
| 11 | 3-methylpyridinium | Phenyl | phenyl | CH3 |
| 12 | 3-methylpyridinium | 3-methylpyridinium | 3-methylpyridinium | 3-methylpyridinium |
| 13 | 4-phenyl-N-methylpyridinium-4-yl | 4-phenyl-4-methylpyridinium | H | H |
| 14 | 4-phenyl-3-methylpyridinium | 4-phenyl-3-methylpyridinium | phenyl | phenyl |
| 15 | 4-phenyl-4-methylpyridinium | phenyl | phenyl | H |
| 16 | 4-phenyl-3-methylpyridinium | Phenyl | Phenyl | H |

TABLE 2

Ras-Raf inhibition of Representative Compounds 1, 12, 4 and 10

|  |  | 10 uM | 50 uM | 100 uM |
|---|---|---|---|---|
| Kobe0065 | Ras pulldown | 0 | 76% |  |
|  | ELIZA | 66.8% | 73.11% |  |
| Representative Compound 1 (purchased) | Ras pulldown | 0 | 76.5% |  |
|  | ELIZA | 34.61% | 35.73% |  |
| Representative Compound 12 (Purchased) | Ras Pulldown | 100% | 68% | 20% |
|  | ELIZA | 0 | 55% |  |
| Representative Compound 4 | ELIZA | 70.54% | 62.74% |  |
| Representative Compound 10 | ELIZA | 35.2% | 13.4% |  |

TABLE 3

| Organ/Tissue | Tumor Type | H-ras | N-ras | K-ras |
|---|---|---|---|---|
| Binary tract | Adenocarcinoma | 0 (151) | 2 (194) | 35 (934) |
| Bladder | Transitional cell carcinoma | 12 (1166) | 2 (322) | 4 (427) |
| Breast | Carcinoma | 1 (542) | 2 (330) | 4 (544) |
| Cervic | Adenocarcinoma | 9 (240) | 3 (64) | 8 (511) |
| Colon | Adenocarcinoma | 0 (76) | 2 (55) | 36 (4310) |
|  | Adenoma | 0 (3) | 0 (11) | 22 (3545) |
| Ganglia | Neuroblastoma | 0 (64) | 8 (105) | 9 (63) |
| (autonomic) | Other | N/A | N/A | 27 (296) |
| Leukemias | AML | 0 (1216) | 12 (3404) | 4 (1778) |
|  | GML | 0 (265) | 3 (532) | 2 (213) |
|  | CMML | 1 (118) | 15 (157) | 11 (84) |
|  | JMML | 0 (41) | 19 (165) | 7 (143) |
| Lymphomas | ALL | 0 (264) | 10 (703) | 7 (549) |
|  | Burkin's lymphoma | 0 (30) | 10 (30) | 3 (30) |
|  | Hodgkin's lymphoma | 2 (44) | 16 (45) | 0 (44) |
|  | Plasma cell myolema | 2 (185) | 20 (484) | 6 (403) |
| Liver | Hepitocellular carcinoma | 0 (163) | 4 (202) | 4 (307) |
| Lung | Large cell carcinoma | 4 (50) | 4 (45) | 21 (189) |
|  | Non small cell carcinoma | 0 (683) | 1 (695) | 16 (3575) |
|  | Squamous cell carcinoma | 1 (261) | 0 (360) | 6 (1407) |
|  | Other (neoplasia) | N/A | N/A | 22 (563) |
| Pancreas | Duclet adenocarcinomas | 0 (110) | 1 (138) | 69 (3483) |
|  | Endocrine tumor | 0 (2) | 75 (4) | 1 (68) |
| Prostate | Adenocarcinoma | 6 (489) | 2 (506) | 8 (1002) |
| Skin | Basal cell carcinoma | 7 (180) | 1 (147) | 4 (147) |
|  | Squamous cell carcinoma | 9 (235) | 7 (107) | 5 (107) |
|  | Malignant melanoma | 1 (904) | 20 (3466) | 2 (924) |
| Soft tissue | Angiocarcinoma | 0 (6) | 0 (6) | 49 (53) |
|  | Leiomycocarcinoma | 3 (30) | 0 (13) | 8 (173) |
|  | Lipocarcinoma | 6 (72) | 0 (21) | 4 (45) |
|  | Rhadomyocarcinoma | 4 (158) | 11 (151) | 4 (162) |
|  | Mycoma | 0 (19) | 0 (19) | 11 (19) |
|  | Malignant florous histiccyloma-pleomorphic sarcoma | 15 (117) | 2 (57) | 16 (131) |
| Stomach | Adenocarcinoma | 4 (218) | 2 (205) | 6 (2054) |
|  | Other | 11 (9) | 0 (1) | 6 (241) |
| Testis | Germinoma | 0 (56) | 7 (115) | 7 (190) |
|  | Serminoma | 17 (30) | 0 (30) | 0 (23) |
| Thyroid | Anaplastic carcinoma | 4 (440) | 17 (436) | 0 (433) |
|  | Folicular carcinoma | 5 (381) | 17 (392) | 4 (372) |
|  | Papillary carcinoma | 2 (1525) | 4 (1941) | 2 (1654) |
|  | Hurthle cell carcinoma | 16 (44) | 4 (26) | 0 (41) |

Note:
Data obtained from the Sangar Catalogue of Somatic Mutations in Cancer, all http://sangar.acidic/genetics/CGP/costmic/
"Values percented as the total percentage of critical samples analyzed (n shown within parentheses) for that particular tumor type.
Boldface corresponds to tumors presenting sigificantly high ratio (>10) of mutation in ras genes.
ALL = acute lymphoblastic leukemia;
AML = acute myelogenicacid leukemia;
CML = chronic myeloid leukemia;
CMML = chronic myelicmonocytic leukemia;
JMML = juvenile myelicmonocytic myeloid leukemia;
N/A = not available

The invention claimed is:

1. A compound selected from the group consisting of compounds of formula (I), or a pharmaceutically acceptable salt thereof:

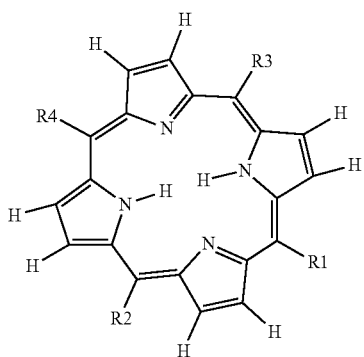

formula (I)

| Compound | R4 | R3 | R2 | R1 |
|---|---|---|---|---|
| 6 | methylpyridinium-4-yl | methylpyridinium-4-yl | CH=CH2—CH3 | CH=CH2—CH3 |
| 7 | methylpyridinium-4-yl | methylpyridinium-4-yl | OH | OH |
| 8 | methylpyridinium-4-yl | Phenyl | phenyl | H |
| 9 | methylpyridinium-4-yl | Phenyl | phenyl | CH3 |
| 10 | methylpyridinium-3-yl | Phenyl | phenyl | H |
| 11 | methylpyridinium-3-yl | Phenyl | phenyl | CH3 |
| 15, and | 3-phenyl-N-methylpyridinium-4-yl | phenyl | phenyl | H |
| 16 | 4-phenyl-N-methylpyridinium-3-yl | Phenyl | Phenyl | H |

2. The compound of claim 1 wherein any two neighbouring R groups are identical.

3. The compound of claim 1 wherein the compound of formula (I) comprises far-infrared absorption spectroscopic properties to absorb far-infrared light penetrating through skin to tumour cells.

4. The compound of claim 1 wherein the compound of formula (I) blocks Ras-Raf interaction.

5. The compound of claim 1 wherein the compound of formula (I) disrupts Ras-dependent signalling.

6. The compound of claim 1 wherein the compound of formula (I) specifically targets oncogenic Ras protein in human tumour cells.

7. A pharmaceutical composition comprising an effective amount of the compound of claim 1, and a pharmaceutically acceptable carrier, diluent and/or excipient.

* * * * *